US006413738B1

(12) United States Patent
Thomas et al.

(10) Patent No.: US 6,413,738 B1
(45) Date of Patent: Jul. 2, 2002

(54) **HOUSE DUST MITE ALLERGEN, *DER F* VII, AND USES THEREFOR**

(75) Inventors: Wayne Robert Thomas, Nedlands (AU); Kaw-Yan Chua, Taipei (TW)

(73) Assignee: ImmuLogic Pharmaceutical Corporation, Waltham, MA (US)

( * ) Notice: Subject to any disclaimer, the term of this patent is extended or adjusted under 35 U.S.C. 154(b) by 0 days.

(21) Appl. No.: 08/553,336

(22) PCT Filed: Mar. 11, 1994

(86) PCT No.: PCT/AU94/00117

§ 371 (c)(1),
(2), (4) Date: Jun. 10, 1996

(87) PCT Pub. No.: WO94/20614

PCT Pub. Date: Sep. 15, 1994

Related U.S. Application Data

(63) Continuation-in-part of application No. 08/081,540, filed on Jun. 22, 1993, which is a continuation-in-part of application No. 08/031,141, filed on Mar. 12, 1993, now abandoned.

(51) Int. Cl.$^7$ ............................ C12P 21/06; A61K 39/35; A61K 38/00; C07K 1/00

(52) U.S. Cl. ...................... 435/69.1; 424/275.1; 514/2; 530/333; 530/350; 530/868; 536/21.3; 536/21.5

(58) Field of Search ............................... 530/300, 350, 530/868, 333; 424/184.1, 185, 192.1, 275.1, 276.1; 536/23.1, 23.5; 435/69.1; 514/2

(56) References Cited

U.S. PATENT DOCUMENTS 4,745,051 A  5/1988  Smith et al.
5,077,214 A  12/1991 Guarino et al.

FOREIGN PATENT DOCUMENTS

EP          0 473 111 A2     3/1992

OTHER PUBLICATIONS

Jobling et al, Mol. Microbiol., 5(7): 1755–67, 1991.*
Canbell in Laboratory Techniques in Biochemistry & Molecular Biology, pp. 1–49, Elesvier, 1991.*
Kahan, Cur. Opin. Immunol., 1992, p. 558, col.–2, 1992.*
Rudinger et al in "Peptide Hormones" ed. Parsons, J.A. University Park Press Inc pp. 1–6, 1976.*
Burgess et al, The Journal of Cell Biology 111: 2129–2138, 1990.*
Lazar et al, Molecular and Cellular Biology, 8(3): 1247–1252, 1988.*
Abe et al, (1987) *Allergy* 42:352–58.
Baldo et al, (1989) "Toward a Definition of the 'Complete' Spectrum and Rank Order of Importance of the Allergens from the House Dust Mite: Dermatophagoides Pteronyssinus", *Adv. Bioscience* 74:13–31.

Bengtsson et al, (1986) "Detection of Allergens in Mould and Mite Preparations by a Nitrocellulose Electroblotting Technique", *Int. Arch. Allergy Appl. Immun.* 80:383–390.
Bowie et al, (Mar. 1990) *Science* 247:1306–1310.
Chapman et al, (1980) "Purification and Characterization of the Major Allergen from Dermatophagoides Pteronyssinus–Antigen P1", *Journal of Immunol.* 125(2):587–592.
Chiba et al, (1990) "Experimental Cedar Pollinosis in Rhesus Monkeys", *Int. Arch. Allergy Appl. Immunol.* 93:83–88.
Chua et al, (1990) *Int. Archs. Allergy Appl. Immunol.* 91:118–123.
Chua et al, (1990) "Expression of Dermatophagoides Pteronyssinus Allergen, Der p II, in *Escherichia coli* and the Binding Studies with Human IgE", *Int. Arch. Allergy Appl. Immunol.* 91:124–129.
Ford et al, (1989) "The Spectrum of Low Molecular Weight House Dust Mite (Dermatophagoides Pteronyssinus) Allergens with Emphasis on Der p II", *Clinical and Experimental Allergy* 20(1):27–31.
Greene et al, (1992) "IgE Binding Structures of the Major House Dust Mite Allergen Der p I", *Molecular Immunol.* 29(2):257–262.
Greene et al. (1990) "Antigenic Analysis of Group I House Dust Mite Allergens Using Random Fragments of Der p I Expressed by Recombinant DNA Libraries", *Int. Arch. Appl. Allergy Immunol.* 92:30–38.
King et al, (1976) "Chemical and Biological Properties of Some Atopic Allergens", *Advances in Immunol.* 23:77–105.
Kohmoto et al, (1991) "Activation of the Kallikrein–Kinin System in Human Plasma by a Scrine Protease from Mites", *Journal Clin. Biochem. Nutr.* 10:15–20.
Lind, (1985) "Purification And Partial Characterization Of Two Major Allergens From The House Dust Mite Dermatophagoides Pteronyssinus", *Journal of Allerg. and Clin. Immunol.* 76(5):753–761.

(List continued on next page.)

*Primary Examiner*—Patricia A. Duffy
(74) *Attorney, Agent, or Firm*—Lahive & Cockfield, LLP; Jane E. Remillard, Esquire; Jeanne M. DiGiorgio., Esq.

(57) ABSTRACT

Isolated nucleic acids encoding allergens of the species *Dermatophagoides pteronyssinus* and *Dermatophagoides farinae*, Der p VII and Der f VII, respectively, are disclosed. A cDNA encoding a peptide having a Der p VII activity and a predicted molecular weight of about 22, 177 daltons is described. A cDNA encoding a peptide having Der f VII activity is also described. The nucleic acids of the invention can be used as probes to detect the presence of Der p VII or Der f VII nucleic acid in a sample or for the recombinant production of peptides having a Der p VII or Der f VII activity. Peptides having a Der p VII or Der f VII activity can be used in compositions suitable for pharmaceutical administration or methods of diagnosing sensitivity to house dust mite allergens.

9 Claims, 9 Drawing Sheets-

OTHER PUBLICATIONS

Lind et al, (1983) "Identification of Allergens in Dermatophagoides Pteronyssinus Mite Body Exract by Crossed Radioimmunoelectrophoresis with Two Different Rabbit Antibody Pools", *Scand. J. Immunol.* 17:263–273.

Stewart et al, (1992) "The Group III Allergen From the House Dust Mite Dermatophagoides Pteronyssinus is a Trypsin–Like Enzyme", *Immunol.* 75:29–35.

Stewart et al, (1988) "Standardization of Rye–Grass Pollen (Lolium Perenne) Extract", *Int. Arch. Allergy Appl. Immun.* 86:9–18.

Stewart et al, (1980) Ajebak 58(Pt 3):259–274.

Stewart et al, (1982) *Int. Archs. Allergy Appl. Immunol.* 69:224–230.

Thomas et al, (1988) "Cloning and Expression of DNA Coding for the Major House Dust Mite Allergen Der p I in *Escherichia Coli* ", *Int. Arch. Allergy Appl. Immun.* 85:127–129.

Tovey et al, (1987) "Comparison by Electroblotting of IgE–Binding Components in Extracts of House Dust Mite Bodies and Spent Mite Culture", *Journal of Allergy and Clin. Immunol.* 79(1):93–102.

Tovey et al, (1989) "The Cloning of a Mite (Dermatophagoides Pteronyssinus) Recombinant Protein that Shares IgE—Binding Determinants with a 14–15 KD Component of Mite Extracts", *Advances in Biosciences* 74:33–43.

Van der Zee et al, (1988) "Skin Tests and Histamine Release with P1–Depleted Dermatophagoides Pteronyssinus Body Extracts and Purified P1", *Journal of Allergy and Clin. Immunol.* 81(5):884–896.

Yuuki, et al, (1991) "Cloning and Expression of cDNA Coding for the Major House Dust Mite Allergen Derf II in *Escherichia Coli*", *Agric. Biol. Chem.* 55(5):1233–1238.

Shen, H. et al., "Molecular cloning of a house dust mite allergen with common antibody binding specificites with multiple components in mite extracts", *Clinical and Experimental Allergy*, vol. 23, pp. 934–940 (1993).

* cited by examiner

```
TTTTTTTTTTTTTGGTTATTCCCATTTTTTTCATATCGTAAAAATCCAAATTCACTTTT  60

TTACCAA ATG ATG AAA TTA TTA TTG ATT GCT GCC GCA GCT TTT GTT  106
        Met Met Lys Leu Leu Leu Ile Ala Ala Ala Ala Phe Val

GCC GTT TCG GCT GAT CCA ATT CAC TAT GAT AAA ATC ACC GAA GAA  151
Ala Val Ser Ala Asp Pro Ile His Tyr Asp Lys Ile Thr Glu Glu

ATT AAC AAA GCT GTT GAT GAA GCC GTC GCT GCA ATT GAA AAA TCC  196
Ile Asn Lys Ala Val Asp Glu Ala Val Ala Ala Ile Glu Lys Ser

GAA ACA TTC GAT CCA ATG AAG GTA CCC GAT CAT TCT GAT AAA TTC  241
Glu Thr Phe Asp Pro Met Lys Val Pro Asp His Ser Asp Lys Phe

GAA CGA CAT ATT GGT ATC ATC GAT TTA AAA GGT GAA TTA GAC ATG  286
Glu Arg His Ile Gly Ile Ile Asp Leu Lys Gly Glu Leu Asp Met

CGA AAC ATT CAA GTT CGA GGA TTA AAA CAA ATG AAA CGT GTA GGT  331
Arg Asn Ile Gln Val Arg Gly Leu Lys Gln Met Lys Arg Val Gly

GAT GCT AAT GTG AAA AGT GAA GAT GGT GTT GTC AAA GCT CAT TTG  376
Asp Ala Asn Val Lys Ser Glu Asp Gly Val Val Lys Ala His Leu

TTG GTC GGT GTT CAT GAT GAC GTT GTT TCA ATG GAA TAT GAT TTA  421
Leu Val Gly Val His Asp Asp Val Val Ser Met Glu Tyr Asp Leu

GCA TAC AAA TTG GGT GAT CTT CAT CCA AAC ACT CAT GTC ATT TCG  466
Ala Tyr Lys Leu Gly Asp Leu His Pro Asn Thr His Val Ile Ser

GAT ATT CAG GAT TTT GTT GTC GAA TTA TCG CTC GAA GTT AGC GAA  511
Asp Ile Gln Asp Phe Val Val Glu Leu Ser Leu Glu Val Ser Glu

GAA GGT AAT ATG ACA TTG ACA TCG TTC GAA GTA CGT CAA TTT GCC  556
Glu Gly Asn Met Thr Leu Thr Ser Phe Glu Val Arg Gln Phe Ala

AAT GTT GTC AAT CAT ATT GGT GGT CTT TCA ATT TTG GAT CCA ATT  601
Asn Val Val Asn His Ile Gly Gly Leu Ser Ile Leu Asp Pro Ile

TTC GCT GTC TTA TCC GAT GTT TTG ACC GCT ATT TTC CAG GAT ACC  646
Phe Ala Val Leu Ser Asp Val Leu Thr Ala Ile Phe Gln Asp Thr

GTA CGT GCA GAA ATG ACC AAA GTA TTG GCA CCA GCA TTC AAA AAA  691
Val Arg Ala Glu Met Thr Lys Val Leu Ala Pro Ala Phe Lys Lys

GAA TTG GAA CGA AAC AAC CAA TAGACTTACACACAACATAACACTGTTATTT  743
Glu Leu Glu Arg Asn Asn Gln

TTACACTGGATAATCAAATGAAATAAATTTTTTTATCATTTTGTTTAAAAAAAAAAAA  802
AAAAAAAAAA  812
```

Fig. 3

```
GATCTTATATCAATAACAATCCAAAAAAACATATCTTACAAAATG ATG AAA TTT TTG   57
                                              Met Met Lys Phe Leu

TTG ATT GCT GCC GTG GCA TTT GTC GCC GTT TCG GCT GAT CCA ATT   102
Leu Ile Ala Ala Val Ala Phe Val Ala Val Ser Ala Asp Pro Ile

CAC TAT GAT AAA ATC ACC GAA CAA ATC AAC AAA GCT ATT GAT GAT   147
His Tyr Asp Lys Ile Thr Glu Gln Ile Asn Lys Ala Ile Asp Asp

GCC ATT GCT GCT ATT GAA CAA TCC CAA ACA ATA GAT CCA ATG AAA   192
Ala Ile Ala Ala Ile Glu Gln Ser Gln Thr Ile Asp Pro Met Lys

GTA CCT GAT CAT GCC GAT AAA TTC GAA CGT CAT GTT GGT ATT GTG   237
Val Pro Asp His Ala Asp Lys Phe Glu Arg His Val Gly Ile Val

GAT TTC AAA GGT GAA TTA GCC ATG CGA AAC ATT GAG GCT CGA GGA   282
Asp Phe Lys Gly Glu Leu Ala Met Arg Asn Ile Glu Ala Arg Gly

TTG AAA CAA ATG AAA CGT CAA GGT GAT GCT AAT CTC AAA GGT GAA   327
Leu Lys Gln Met Lys Arg Gln Gly Asp Ala Asn Val Lys Gly Glu

GAG GGT ATT GTT AAA GCT CAT TTG TTG ATC GGT GTT CAC GAT GAT   372
Glu Gly Ile Val Lys Ala His Leu Leu Ile Gly Val His Asp Asp

ATC GTC TCG ATG GAA TAT GAT TTA GCA TAC AAA TTG GGT GAT CTT   417
Ile Val Ser Met Glu Tyr Asp Leu Ala Tyr Lys Leu Gly Asp Leu

CAT CCA ACC ACT CAT GTC ATT TCG GAT ATT CAA GAT TTT GTT CTT   462
His Pro Thr Thr His Val Ile Ser Asp Ile Gln Asp Phe Val Val

GCC TTG TCC CTT GAA ATT TCT GAT GAA GGT AAC ATA ACA ATG ACA   507
Ala Leu Ser Leu Glu Ile Ser Asp Glu Gly Asn Ile Thr Met Thr

TCT TTT GAA GTA CGA CAA TTC GCT AAT GTT GTC AAC CAT ATT GGT   552
Ser Phe Glu Val Arg Gln Phe Ala Asn Val Val Asn His Ile Gly

GGT CTT TCA ATC TTG GAT CCA ATT TTT GGC GTT TTA TCT GAT GTA   597
Gly Leu Ser Ile Leu Asp Pro Ile Phe Gly Val Leu Ser Asp Val

TTG ACC GCT ATT TTC CAA GAC ACC GTA CGT AAG GAA ATG ACC AAA   642
Leu Thr Ala Ile Phe Gln Asp Thr Val Arg Lys Glu Met Thr Lys

GTA TTG CCA CCA GCA TTT AAA CGT GAA TTG GAA AAA AAT TAACCAA   688
Val Leu Ala Pro Ala Phe Lys Arg Glu Leu Glu Lys Asn

TAGACATCATTTTTCCAACTGTACAATCTCTATTTCACTGACAATAAAATAAAATTTTT   747

ATTTTTATTTCTCC    761
```

Fig. 6

```
Dp VII: TTTTTTTTTTTTTTGGTTATTCCCATTTTTTTCATATCGTAAAAATCCAAAT        52

Df VII:                         GA.C..AT..CAATA.C..TC.A...A        27

Dp VII: TCACTTTTTTACCAA ATG ATG AAA TTA TTA TTG ATT GCT GCC         94
                        Met Met Lys Leu Leu Leu Ile Ala Ala

Df VII: AACA.A.C....A..  ... ... ...  ..T ..G ... ... ... ...       69
                                         Phe

Dp VII: GCA GCT TTT GTT GCC GTT TCG GCT GAT CCA ATT CAC TAT        133
        Ala Ala Phe Val Ala Val Ser Ala Asp Pro Ile His Tyr

Df VII: .TG ..A ... ..C ... ... ... ... ... ... ... ... ...        108
        Val

Dp VII: GAT AAA ATC ACC GAA GAA ATT AAC AAA GCT GTT GAT GAA        172
        Asp lys Ile Thr Glu Glu Ile Asn Lys Ala Val Asp Glu Df VII: ... ... ... ... ... ... ..C ... ... ... A.. ... ..T        147
                                                 Ile         Asp Dp VII: GCC GTC GCT CCA ATT GAA AAA TCC GAA ACA TTC GAT CCA        211
        Ala Val Ala Ala Ile Glu Lys Ser Glu Thr Phe Asp Pro Df VII: ... A.T ... ..T ... ... C.. ... ... ... A.A ... ...        186
            Ile             Gln                 Ile Dp VII: ATG AAG GTA CCC GAT CAT TCT GAT AAA TTC GAA CGA CAT        250
        Met Lys Val Pro Asp His Ser Asp Lys Phe Glu Arg His Df VII: ... ..A ... ..T ... ... G.C ... ... ... ... ..T ...        225
                                Ala Dp VII: ATT GGT ATC ATC GAT TTA AAA GGT GAA TTA GAC ATG CGA        289
        Ile Gly Ile Ile Asp Leu Lys Gly Glu Leu Asp Met Arg Df VII: G.. ... ..T G.G ... ..C ... ... ... ... .C. ... ...        264
        Val     Val Phe                         Ala
```

Fig. 7A

```
Dp VII: AAC ATT CAA GTT CGA GCA TTA AAA CAA ATG AAA CGT GTA   328
        Asn Ile Gln Val Arg Gly Leu Lys Gln Met Lys Arg Val

Df VII: ... ... G.G .C. ... ... ..G ... ... ... ... ... CA.   303
                Glu Ala                                 Gln

Dp VII: GGT GAT GCT AAT GTG AAA AGT GAA GAT GGT GTT GTC AAA   367
        Gly Asp Ala Asn Val Lys Ser Glu Asp Gly Val Val Lys

Df VII: ... ... ... ... ..C ... G.. ... ..G ... A.. ..T ...   342
                            Gly     Glu     Ile

Dp VII: GCT CAT TTG TTG GTC GGT GTT CAT GAT GAC GTT GTT TCA   406
        Ala His Leu Leu Val Gly Val His Asp Asp Val Val Ser

Df VII: ... ... ... ... A.. ... ... ... ..C ... ..T A.C ..C ..G   381
                        Ile                         Ile

Dp VII: ATG GAA TAT GAT TTA GCA TAC AAA TTG CCT GAT CTT CAT   445
        Met Glu Tyr Asp Leu Ala Tyr Lys Leu Gly Asp Leu His

Df VII: ... ... ... ... ... ... ... ... ... ... ... ... ...   420

Dp VII: CCA AAC ACT CAT GTC ATT TCG GAT ATT CAG GAT TTT GTT   484
        Pro Asn Thr His Val Ile Ser Asp Ile Gln Asp Phe Val

Df VII: ... .C. ... ... ... ... ... ... ... ..A ... ... ...   459
            Thr

Dp VII: GTC GAA TTA TCG CTC GAA GTT AGC GAA GAA GGT AAT ATG   523
        Val Glu Leu Ser Leu Glu Val Ser Glu Glu Gly Asn Met

Df VII: ..T .CC ..G ..C ..T ... A.. TCT ..T ... ... ..C ...A   498
            Ala                 Ile     Asp             Ile

Dp VII: ACA TTG ACA TCG TTC GAA GTA CGT CAA TTT CCC AAT GTT   562
        Thr Leu Thr Ser Phe Glu Val Arg Gln Phe Ala Asn Val

Df VII: ... A.. ... ..T ..T ... ... ..A ... ..C ..T ... ...   537
            Met
```

Fig. 7B

```
Dp VII: GTC AAT CAT ATT GGT GGT CTT TCA ATT TTG GAT CCA ATT   601
        Val Asn His Ile Gly Gly Leu Ser Ile Leu Asp Pro Ile

Df VII: ... ..C ... ... ... ... ... ... ..C ... ... ... ...   576

Dp VII: TTC GCT GTC TTA TCC GAT GTT TTG ACC GCT ATT TTC CAG   640
        Phe Ala Val Leu Ser Asp Val Leu Thr Ala Ile Phe Gln

Df VII: ..T .GC ..T ... ..T ... ..A ... ... ... ... ... ..A   615
            Gly

Dp VII: GAT ACC GTA CGT CCA GAA ATG ACC AAA GTA TTG GCA CCA   679
        Asp Thr Val Arg Ala Glu Met Thr Lys Val Leu Ala Pro

Df VII: ..C ... ... ... AAG ... ... ... ... ... ... ... ...   654
                        Lys

Dp VII: GCA TTC AAA AAA GAA TTG GAA CGA AAC AAC CAA TAGACTT   719
        Ala Phe Lys Lys Glu Leu Glu Arg Asn Asn Gln

Df VII: ... ..T ... CGT ... ... ... AA. ..T        ..AC.AA   688
                    Arg                Lys

Dp VII: ACACACAACATAACACTGTTATTTTTACACTGGATAATCAAATGAAATAAA    770

Df VII: TAGACATCAT.TTTC.AAC.G.ACAAT.T..ATT.C.CTG.CAAT..A.T.    739

Dp VII: TTTTTTTATCATTTTGTTTAAAAAAAAAAAAAAAAAAAAAAA            812

Df VII: AAA....TATT...AT..CTCC                                 761
```

Fig. 7C

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 812 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 68..712

(ix) FEATURE:
      (A) NAME/KEY: mat_peptide
      (B) LOCATION: 119..712

(xi) SEQUENCE DESCRIPTION: SEQ ID NO:1:

```
TTTTTTTTTT TTTTGGTTAT TCCCATTTTT TTCATATCGT AAAAATCCAA ATTCACTTTT        60

TTACCAA ATG ATG AAA TTA TTA TTG ATT GCT GCC GCA GCT TTT GTT GCC        109
        Met Met Lys Leu Leu Leu Ile Ala Ala Ala Ala Phe Val Ala
         -1          -5                 -10

GTT TCG GCT GAT CCA ATT CAC TAT GAT AAA ATC ACC GAA GAA ATT AAC        157
Val Ser Ala Asp Pro Ile His Tyr Asp Lys Ile Thr Glu Glu Ile Asn
-15          1               5                  10

AAA GCT GTT GAT GAA GCC GTC GCT GCA ATT GAA AAA TCC GAA ACA TTC        205
Lys Ala Val Asp Glu Ala Val Ala Ala Ile Glu Lys Ser Glu Thr Phe
     15                  20                  25

GAT CCA ATG AAG GTA CCC GAT CAT TCT GAT AAA TTC GAA CGA CAT ATT        253
Asp Pro Met Lys Val Pro Asp His Ser Asp Lys Phe Glu Arg His Ile
 30              35                  40                  45

GGT ATC ATC GAT TTA AAA GGT GAA TTA GAC ATG CGA AAC ATT CAA GTT        301
Gly Ile Ile Asp Leu Lys Gly Glu Leu Asp Met Arg Asn Ile Gln Val
             50                  55                  60

CGA GGA TTA AAA CAA ATG AAA CGT GTA GGT GAT GCT AAT GTG AAA AGT        349
Arg Gly Leu Lys Gln Met Lys Arg Val Gly Asp Ala Asn Val Lys Ser
             65                  70                  75

GAA GAT GGT GTT GTC AAA GCT CAT TTG TTG GTC GGT GTT CAT GAT GAC        397
Glu Asp Gly Val Val Lys Ala His Leu Leu Val Gly Val His Asp Asp
             80                  85                  90

GTT GTT TCA ATG GAA TAT GAT TTA GCA TAC AAA TTG GGT GAT CTT CAT        445
Val Val Ser Met Glu Tyr Asp Leu Ala Tyr Lys Leu Gly Asp Leu His
         95                  100                 105

CCA AAC ACT CAT GTC ATT TCG GAT ATT CAG GAT TTT GTT GTC GAA TTA        493
Pro Asn Thr His Val Ile Ser Asp Ile Gln Asp Phe Val Val Glu Leu
110                 115                 120                 125

TCG CTC GAA GTT AGC GAA GAA GGT AAT ATG ACA TTG ACA TCG TTC GAA        541
Ser Leu Glu Val Ser Glu Glu Gly Asn Met Thr Leu Thr Ser Phe Glu
                130                 135                 140

GTA CGT CAA TTT GCC AAT GTT GTC AAT CAT ATT GGT GGT CTT TCA ATT        589
Val Arg Gln Phe Ala Asn Val Val Asn His Ile Gly Gly Leu Ser Ile
            145                 150                 155

TTG GAT CCA ATT TTC GCT GTC TTA TCC GAT GTT TTG ACC GCT ATT TTC        637
Leu Asp Pro Ile Phe Ala Val Leu Ser Asp Val Leu Thr Ala Ile Phe
                160                 165                 170
```

```
CAG GAT ACC GTA CGT GCA GAA ATG ACC AAA GTA TTG GCA CCA GCA TTC    685
Gln Asp Thr Val Arg Ala Glu Met Thr Lys Val Leu Ala Pro Ala Phe
    175                 180                 185

AAA AAA GAA TTG GAA CGA AAC AAC CAA TAGACTTACA CACAACATAA           732
Lys Lys Glu Leu Glu Arg Asn Asn Gln
190             195

CACTGTTATT TTTACACTGG ATAATCAAAT GAAATAAATT TTTTTATCAT TTTGTTTAAA   792

AAAAAAAAAA AAAAAAAAA                                                812
```

(2) INFORMATION FOR SEQ ID NO:2:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:2:

```
Met Met Lys Leu Leu Leu Ile Ala Ala Ala Phe Val Ala Val Ser
 -1          -5                  -10                 -15

Ala Asp Pro Ile His Tyr Asp Lys Ile Thr Glu Glu Ile Asn Lys Ala
      1             5                  10                  15

Val Asp Glu Ala Val Ala Ala Ile Glu Lys Ser Glu Thr Phe Asp Pro
                 20                  25                  30

Met Lys Val Pro Asp His Ser Asp Lys Phe Glu Arg His Ile Gly Ile
             35                  40                  45

Ile Asp Leu Lys Gly Glu Leu Asp Met Arg Asn Ile Gln Val Arg Gly
         50                  55                  60

Leu Lys Gln Met Lys Arg Val Gly Asp Ala Asn Val Lys Ser Glu Asp
     65                  70                  75

Gly Val Val Lys Ala His Leu Leu Val Gly Val His Asp Asp Val Val
 80                  85                  90                  95

Ser Met Glu Tyr Asp Leu Ala Tyr Lys Leu Gly Asp Leu His Pro Asn
                100                 105                 110

Thr His Val Ile Ser Asp Ile Gln Asp Phe Val Val Glu Leu Ser Leu
            115                 120                 125

Glu Val Ser Glu Glu Gly Asn Met Thr Leu Thr Ser Phe Glu Val Arg
        130                 135                 140

Gln Phe Ala Asn Val Val Asn His Ile Gly Gly Leu Ser Ile Leu Asp
    145                 150                 155

Pro Ile Phe Ala Val Leu Ser Asp Val Leu Thr Ala Ile Phe Gln Asp
160                 165                 170                 175

Thr Val Arg Ala Glu Met Thr Lys Val Leu Ala Pro Ala Phe Lys Lys
                180                 185                 190

Glu Leu Glu Arg Asn Asn Gln
                195
```

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO:3:

GATCCAATTC ACTATGAT                                                    18

(2) INFORMATION FOR SEQ ID NO:4:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:4:

GGTGAATTAG ACATGCG                                                     17

(2) INFORMATION FOR SEQ ID NO:5:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:5:

TCAATTTTGG ATCCAATTTT CGCT                                             24

(2) INFORMATION FOR SEQ ID NO:6:

(i) SEQUENCE CHARACTERISTICS:
             (A) LENGTH: 761 base pairs
             (B) TYPE: nucleic acid
             (C) STRANDEDNESS: single
             (D) TOPOLOGY: linear (ii) MOLECULE TYPE: cDNA (ix) FEATURE:
             (A) NAME/KEY: CDS
             (B) LOCATION: 43..681

(xi) SEQUENCE DESCRIPTION: SEQ ID NO:6:

GATCTTATAT CAATAACAAT CCAAAAAAAC ATATCTTACA AA ATG ATG AAA TTT          54
                                              Met Met Lys Phe
                                               1

TTG TTG ATT GCT GCC GTG GCA TTT GTC GCC GTT TCG GCT GAT CCA ATT       102
Leu Leu Ile Ala Ala Val Ala Phe Val Ala Val Ser Ala Asp Pro Ile
 5              10                  15                  20

CAC TAT GAT AAA ATC ACC GAA GAA ATC AAC AAA GCT ATT GAT GAT GCC       150
His Tyr Asp Lys Ile Thr Glu Glu Ile Asn Lys Ala Ile Asp Asp Ala
            25                  30                  35

ATT GCT GCT ATT GAA CAA TCC GAA ACA ATA GAT CCA ATG AAA GTA CCT       198
Ile Ala Ala Ile Glu Gln Ser Glu Thr Ile Asp Pro Met Lys Val Pro
        40                  45                  50

GAT CAT GCC GAT AAA TTC GAA CGT CAT GTT GGT ATT GTG GAT TTC AAA       246
Asp His Ala Asp Lys Phe Glu Arg His Val Gly Ile Val Asp Phe Lys
    55                  60                  65

GGT GAA TTA GCC ATG CGA AAC ATT GAG GCT CGA GGA TTG AAA CAA ATG       294
Gly Glu Leu Ala Met Arg Asn Ile Glu Ala Arg Gly Leu Lys Gln Met
70                  75                  80
```

-continued

```
AAA CGT CAA GGT GAT GCT AAT GTC AAA GGT GAA GAG GGT ATT GTT AAA      342
Lys Arg Gln Gly Asp Ala Asn Val Lys Gly Glu Glu Gly Ile Val Lys
 85                  90                  95                 100

GCT CAT TTG TTG ATC GGT GTT CAC GAT GAT ATC GTC TCG ATG GAA TAT      390
Ala His Leu Leu Ile Gly Val His Asp Asp Ile Val Ser Met Glu Tyr
                    105                 110                 115

GAT TTA GCA TAC AAA TTG GGT GAT CTT CAT CCA ACC ACT CAT GTC ATT      438
Asp Leu Ala Tyr Lys Leu Gly Asp Leu His Pro Thr Thr His Val Ile
                120                 125                 130

TCG GAT ATT CAA GAT TTT GTT GTT GCC TTG TCC CTT GAA ATT TCT GAT      486
Ser Asp Ile Gln Asp Phe Val Val Ala Leu Ser Leu Glu Ile Ser Asp
            135                 140                 145

GAA GGT AAC ATA ACA ATG ACA TCT TTT GAA GTA CGA CAA TTC GCT AAT      534
Glu Gly Asn Ile Thr Met Thr Ser Phe Glu Val Arg Gln Phe Ala Asn
        150                 155                 160

GTT GTC AAC CAT ATT GGT GGT CTT TCA ATC TTG GAT CCA ATT TTT GGC      582
Val Val Asn His Ile Gly Gly Leu Ser Ile Leu Asp Pro Ile Phe Gly
165                 170                 175                 180

GTT TTA TCT GAT GTA TTG ACC GCT ATT TTC CAA GAC ACC GTA CGT AAG      630
Val Leu Ser Asp Val Leu Thr Ala Ile Phe Gln Asp Thr Val Arg Lys
                185                 190                 195

GAA ATG ACC AAA GTA TTG GCA CCA GCA TTT AAA CGT GAA TTG GAA AAA      678
Glu Met Thr Lys Val Leu Ala Pro Ala Phe Lys Arg Glu Leu Glu Lys
            200                 205                 210

AAT TAACCAATAG ACATCATTTT TCCAACTGTA CAATCTCTAT TCACTGACA            731
Asn

ATAAAATAAA ATTTTTATTT TTATTTCTCC                                     761
```

(2) INFORMATION FOR SEQ ID NO:7:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO:7:

```
Met Met Lys Phe Leu Leu Ile Ala Ala Val Ala Phe Val Ala Val Ser
 1               5                  10                  15

Ala Asp Pro Ile His Tyr Asp Lys Ile Thr Glu Glu Ile Asn Lys Ala
                20                  25                  30

Ile Asp Asp Ala Ile Ala Ile Glu Gln Ser Glu Thr Ile Asp Pro
            35                  40                  45

Met Lys Val Pro Asp His Ala Asp Lys Phe Glu Arg His Val Gly Ile
 50                  55                  60

Val Asp Phe Lys Gly Glu Leu Ala Met Arg Asn Ile Glu Ala Arg Gly
 65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
                100                 105                 110

Ser Met Glu Tyr Asp Leu Ala Tyr Lys Leu Gly Asp Leu His Pro Thr
            115                 120                 125

Thr His Val Ile Ser Asp Ile Gln Asp Phe Val Val Ala Leu Ser Leu
        130                 135                 140

Glu Ile Ser Asp Glu Gly Asn Ile Thr Met Thr Ser Phe Glu Val Arg
145                 150                 155                 160
```

Gln Phe Ala Asn Val Val Asn His Ile Gly Gly Leu Ser Ile Leu Asp
                165                 170                 175

Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
    210

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGAATTCGA TCCAATTCAC TATGAT                                    26

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGTGGCGACGACTCCTGGAGCCCG                                    24

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTTTTCCCAGTCACGAC                                            17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GGTGAATTAGACATGCG                                            17

(2) INFORMATION FOR SEQ ID NO:12:

(i) SEQUENCE CHARACTERISTICS:
        (A) LENGTH: 24 base pairs
        (B) TYPE: nucleic acid -continued

```
            (C) STRANDEDNESS: single
            (D) TOPOLOGY: linear (ii) MOLECULE TYPE: cDNA (xi) SEQUENCE DESCRIPTION: SEQ ID NO:12:

TCAATCTTGGATCCAATTTTTGGC                                                    24

(2) INFORMATION FOR SEQ ID NO:13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

GGAATTCTTA ATTTTTTTCC AATTCACG                                              28

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

TTGACACCAGACCAACTGGTAATG                                                    24

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

ATGACGTTCGAATTTATC                                                          18
```

HOUSE DUST MITE ALLERGEN, *DER F* VII, AND USES THEREFOR

RELATED APPLICATIONS

This application claims priority to PCT/AU94/00117 filed on Mar. 11, 1994, which in turn is a continuation-in-part of U.S. Ser. No. 08/803,141 filed on Mar. 12, 1993 (abandoned) which is a continuation in part of U.S. Ser. No. 08/081,540 filed on Jun. 22, 1993 (pending).

BACKGROUND OF INVENTION

Approximately 10% of the population become hypersensitized (allergic) upon exposure to antigens from a variety of environmental sources. Those antigens that induce immediate and/or delayed types of hypersensitivity are known as allergens (King, T. P., (1976) Adv. Immunol., 23:77–105). These include products of grasses, trees, weeds, animal dander, insects, food, drugs, and chemicals. Genetic predisposition of an individual is believed to play a role in the development of immediate allergic responses (Young, R. P. et al., (1990) *Clin. Sci.*, 79:19) such as atopy and anaphylaxis whose symptoms include hay fever, asthma, and hives.

The antibodies involved in atopic allergy belong primarily to the IgE class of immunoglobins. IgE binds to basophils, mast cells and dendritic cells via a specific, high-affinity receptor FcεRI (Kinet, J. P., (1990) *Curr. Opin. Immunol.*, 2:499–505). Upon combination of an allergen acting as a ligand with its cognate receptor IgE, FcεRI bound to the IgE may be cross-linked on the cell surface, resulting in physiological manifestations of the IgE—allergen interaction. These physiological effects include the release of, among other substances, histamine, serotonin, heparin, chemotactic factor(s) for eosinophilic leukocytes and/or leukotrienes C4, D4, and E4, which cause prolonged constriction of bronchial smooth muscle cells (Hood, L. E. et al., *Immunology* (2nd ed.), The Benjamin/Cumming Publishing Co., Inc. (1984)). Hence, the ultimate consequence of the interaction of an allergen with IgE is allergic symptoms triggered by the release of the aforementioned mediators. Such symptoms may be systemic or local in nature, depending on the route of entry of the antigen and the pattern of deposition of IgE on mast cells or basophils. Local manifestations generally occur on epithelial surfaces at the site of entry of the allergen. Systemic effects can induce anaphylaxis (anaphylactic shock) which results from IgE-basophil response to circulating (intravascular) antigen.

Studies with purified allergens have shown that about 80% of patients allergic to the mite *Dermatophagoides pteronyssinus* produce IgE reactive to Der p I and Der p II (Chapman M. D. et al., *J. Immunol.* (1980) 125:587–92; Lind P., *J. Allergy Clin. Immunol.* (1985) 76:753–61; Van derZee J. S. et al., *J. Allergy Clin. Immunol.* (1988) 81:884–95). For about half of the patients, these specificities constitute 50% of the IgE antimite antibody. The allergen Der p III, recently identified as trypsin, (Stewart G. A. et al., *Immunology* (1992) 75:29–35) reacts with a similar or higher frequency (Stewart G. A. et al., supra; Ford S. A. et al., *Clin. Exp. Allergy* (1989) 20:27–31). However, in the only quantitative study performed to date, the investigators reported the level of IgE binding to be considerably less than Der p I. Electrophoretic techniques (Ford S. A. et al, supra; Bengtsson A. et al., *Int. Arch. Allergy Appl. Immunol.* (1986) 80:383–90; Lind P. et al., *Scand. J. Immunol.* (1983) 17:263–73; Tovey E. R. et al, *J. Allergy Clin. Immunol.* (1987) 79:93–102) have shown that most sera recognize other allergens. For example, in the study of Ford et al (supra) Western blotting showed 8 sera reacting with 1–2 bands, 6 with 3–6 and 3 with a greater number including one with at least 13. In another study, Baldo et al. (*Adv. Bioscience* (1989) 4:13–31) report the finding of components at Mr 30, 26, 25K reacting with 50% of sera. To determine the importance of particular specificities in the allergic reactions, purified allergens would be required for quantitative IgE binding tests and to examine the frequency and lymphokine profile for T cell reactivity.

Treatment of patients with sensitivity to house dust mites by administration of increasing doses of house dust extracts has the drawbacks of potential anaphylaxis during treatment and the possible necessity of continuing therapy over a period of several years to build up sufficient tolerance that results in significant diminution of clinical symptoms. A therapeutic composition and method of therapy which avoids these problems would be beneficial.

SUMMARY OF THE INVENTION

This invention provides isolated nucleic acids encoding peptides having at least one biological activity of Der p VII or Der f VII, protein allergens of the species *Dermatophagoides pteronyssinus* and *Dermatophagoides farinae*. Preferred nucleic acids are cDNAs having a nucleotide sequence shown in FIGS. 3A and 3B (SEQ ID NO: 1) (Der p VII) and FIGS. 6A and 6B (SEQ ID NO: 6) (Der f VII). The invention also pertains to peptides encoded by all or a portion of such cDNAs (SEQ ID NO: 1 and SEQ ID NO: 6) and having at least one biological activity of Der p VII or Der f VII. Also contemplated are isolated nucleic acids which hybridize under high stringency conditions (e.g., equivalent to 20–27° C. below Tm and 1M NaCl) to a nucleic acid having a nucleotide sequence shown in FIGS. 3A and 3B (SEQ ID NO: 1) or FIGS. 6A and 6B (SEQ ID NO: 6) or which encodes a peptide comprising all or a portion of an amino acid sequence of FIGS. 3A and 3B (SEQ ID NO: 2)(Der p VII) or FIGS. 6A and 6B (SEQ ID NO: 7)(Der f VII). Nucleic acids which encode peptides having an activity of Der p VII or Der f VII and having at least 50% homology with a sequence shown in FIGS. 3A and 3B (SEQ ID NO: 2)(Der p VII) or FIGS. 6A and 6B (SEQ ID NO: 7)(Der f VII) are also featured. Peptides having a Der p VII or Der f VII activity produced by recombinant expression of a nucleic acid of the invention, and peptides having a Der p VII or Der f VII activity prepared by chemical synthesis are also featured by this invention. Preferred peptides have the ability to induce a T cell response, which may include T cell stimulation (measured by, for example, T cell proliferation or cytokine secretion) or T cell nonresponsiveness (i.e., contact with the peptide or a complex of the peptide with an MHC molecule of an antigen presenting cell induces the T cell to become unresponsive to stimulatory signals or incapable of proliferation). Other preferred peptides, either apart from or in addition to the ability to induce a T cell response, have the ability to bind the dust mite specific IgE of dust mite-allergic subjects. Such peptides are useful in diagnosing sensitivity to dust mite in a subject. Still other peptides, either apart from or in addition to the ability to induce a T cell response, have a significantly reduced ability to bind dust mite-allergic IgE. Such peptides are particularly useful as therapeutic agents.

Other preferred peptides comprise an amino acid sequence shown in FIGS. 3A and 3B (SEQ ID NO: 2) (Der p VII) or FIGS. 6A and 6B (SEQ ID NO: 7) (Der f VII). In one embodiment, peptides having a Der p VII or Der f VII activity and comprising a portion of the amino acid sequence of FIGS. 3A and 3B (SEQ ID NO: 2) or FIGS. 6A and 6B (SEQ ID NO: 7) are featured. Such peptides are at least about 8–30 amino acids in length, preferably about 10–20 amino acids in length, and most preferably about 10–16 amino acids in length.

Another aspect of the invention features antibodies specifically reactive with a peptide having a Der p VII or Der f VII activity. A peptide having an activity of Der p VII or Der f VII can be used in compositions suitable for pharmaceutical administration. Such compositions can be used in a manner similar to dust mite extracts to treat or prevent allergic reactions to a dust mite allergen in a subject. Nucleic acids of the invention and peptides having an activity of Der p VII or Der f VII can also be used for diagnosing sensitivity in a subject to a dust mite allergen.

BRIEF DESCRIPTION OF THE DRAWINGS

FIG. 3 is the nucleotide sequence and deduced amino acid sequence of Der p VII clone HD6.

FIG. 6 is the nucleotide sequence and deduced amino acid sequence of Der f VII.

FIGS. 7A, 7B, and 7C is a comparison of the nucleotide sequence and deduced amino acid sequence of Der f VII and Der p VII. Dots indicate a consensus in nucleotide sequence between Der f VII and Der p VII. Nucleotide bases which differ between Der f VII and Der p VII are indicated, along with any corresponding amino acid differences.

DETAILED DESCRIPTION OF THE INVENTION

Figure 1:
FIG. 1 shows the binding frequency of IgE from allergic sera with λgt11-HD6 plaques.

This invention pertains to isolated nucleic acids encoding peptides having at least one biological activity of Der p VII or Der f VII, allergens of the species Dermatophagoides pteronyssinus and Dermatophagoides farinae, respectively. Preferably, the nucleic acid is a cDNA comprising a nucleotide sequence shown in FIGS. 3A and 3BA and 3B (SEQ ID NO: 1) (Der p VII) or FIGS. 6A and 6BA and 6B (SEQ ID NO:6) (Der f VII).

The cDNA shown in FIGS. 3A and 3BA and 3B (SEQ ID NO: 1) encodes a Der p VII peptide which includes a 17 amino acid leader sequence encoded by base 68 through base 118. This leader sequence is not found in the mature Der p VII protein, which is encoded by bases 119 through 715. The deduced amino acid sequence of Der p VII based on this cDNA is also shown in FIGS. 3A and 3B (SEQ ID NO: 2). The cDNA encodes a 198 residue mature peptide having a predicted molecular weight of 22,177 Da, no cysteines and a single potential N-linked glycosylation site. A host cell transfected with an expression vector containing a nucleotide sequence encoding Der p VII was deposited under the Budapest Treaty with the American Type Culture Collection on Jul. 6, 1993 and assigned accession number 69.348.

The cDNA shown in FIGS. 6A and 6B (SEQ ID NO: 6) encodes a Der f VII peptide. Der f VII peptide is encoded by bases 43 through 681 of this cDNA sequence. The deduced amino acid sequence of Der f VII based on this cDNA is shown in FIGS. 6A and 6B (SEQ ID NO: 7). Similar to Der p VII, this Der f VII peptide may contain a leader sequence not found in the nature protein.

Accordingly, one aspect of this invention pertains to isolated nucleic acids comprising nucleotide sequences encoding Der p VII or Der f VII, fragments thereof encoding peptides having at least one biological activity of Der p VII or Der f VII, and equivalents of such nucleic acids. The term nucleic acid as used herein is intended to include such fragments and equivalents. The term equivalent is intended to include nucleotide sequences encoding functionally equivalent Der p VII or Der f VII proteins or functionally equivalent peptides having an activity of Der p VII or Der f VII. As defined herein, a peptide having an activity of Der p VII or Der f VII has at least one biological activity of the Der p VII or Der f VII allergen. Equivalent nucleotide sequences will include sequences that differ by one or more nucleotide substitutions, additions or deletions, such as allelic variants, and will also include sequences that differ from the nucleotide sequence encoding Der p VII or Der f VII shown in FIGS. 3A and 3B (SEQ ID NO: 1) or FIGS. 6A and 6B (SEQ ID NO: 6) due to the degeneracy of the genetic code. Equivalents will also include nucleotide sequences that hybridize under stringent conditions (i.e., equivalent to about 20–27° C. below melting temperature ($T_m$) and about 1M salt) to the nucleotide sequence of Der p VII shown in FIGS. 3A and 3B (SEQ ID NO: 1) or Der f VII shown in FIGS. 6A and 6B (SEQ ID NO: 6).

Peptides referred to herein as having an activity of Der p VII or Der f VII or having a Der p VII or Der f VII activity are defined herein as peptides that have an amino acid sequence substantially corresponding to all or a portion of the amino acid sequence of Der p VII or Der f VII shown in FIGS. 3A and 3B (SEQ ID NO: 2) or FIGS. 6A and 6B (SEQ ID NO: 7), which peptide has at least one biological activity of Der p VII or Der f VII. For example, a peptide having an activity of Der p VII or Der f VII may have the ability to induce a response in Der p VII or Der f VII restricted T cells such as stimulation (e.g., T cell proliferation or cytokine secretion) or to induce T cell non-responsiveness. Alternatively, or additionally, a peptide having an activity of Der p VII or Der f VII may have the ability to bind (to be recognized by) immunoglobulin E (IgE) antibodies of dust mite-allergic subjects. Peptides which bind IgE are useful in methods of detecting allergic sensitivity to Der p VII or Der f VII in a subject. Peptides that do not bind IgE, or bind IgE to a lesser extent than a purified, native Der p VII or Der f VII protein binds IgE are particularly useful as therapeutic agents.

In one embodiment, the nucleic acid is a cDNA encoding a peptide having an activity of Der p VII or Der f VII. Preferably, the nucleic acid is a cDNA molecule comprising at least a portion of the nucleotide sequence encoding Der p VII shown in FIGS. 3A and 3B (SEQ ID NO: 1) or Der f VII shown in FIGS. 6A and 6B (SEQ ID NO: 6). A preferred portion of the cDNA molecules of FIGS. 3A and 3B and FIGS. 6A and 6B includes the coding region of the molecule.

In another embodiment, the nucleic acid of the invention encodes a peptide having an activity of Der p VII or Der f VII and comprising an amino acid sequence shown in FIG. 3A and 3B (SEQ ID NO:2) (Der p VII) or FIGS. 6A and 6B (SEQ ID NO: 7) (Der f VII). Preferred nucleic acids encode a peptide having a Der p VII or Der f VII activity and having at least about 50% homology, more preferably at least about 60% homology and most preferably at least about 70% homology with the sequence shown in FIGS. 3A and 3B (SEQ ID NO: 1) (Der p VII) or FIGS. 6A and 6B (SEQ ID NO: 6) (Der f VII). Nucleic acids which encode peptides having a Der p VII or Der f VII activity and having at least about 90%, more preferably at least about 95%, and most preferably at least about 98–99% homology with a sequence set forth in FIGS. 3A and 3B (SEQ ID NO: 2) (Der p VII) or FIGS. 6A and 6B (SEQ ID NO: 7) (Der f VII) are also within the scope of the invention. Homology refers to sequence similarity between two peptides having an activity of Der p VII or Der f VII or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in FIGS. 3A and 3B (SEQ ID NO: 2) (Der p VII) or FIGS. 6A and 6B (SEQ ID NO: 7) (Der f VII). Appropriate stringency conditions which promote DNA hybridization, for example, 6.0+ sodium chloride/sodium citrate (SSC) at about 45° C., followed by a wash of 2.0×SSC at 500 are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding peptides having an activity of Der p VII or Der f VII, as described herein, and having a sequence which differs from the nucleotide sequences shown in FIGS. 3A and 3B (SEQ ID NO: 1) and FIGS. 6A and 6B (SEQ ID NO: 6) due to degeneracy in the genetic code are also within the scope of the invention. Such nucleic acids encode functionally equivalent peptides (i.e., a peptide having an activity of Der p VII or Der f VII) but differ in sequence from the sequences of FIGS. 3A and 3B and FIGS. 6A and 6B due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the Der p VII or Der f VII protein. However, it is expected that DNA sequence polymorphisms that do lead to changes in the amino acid sequence of Der p VII or Der f VII will exist within the dust mite population. One skilled in the art will appreciate that these variations in one or more nucleotides (up to about 3–4% of the nucleotides) of the nucleic acids encoding peptides having an activity of Der p VII or Der f VII may exist among individual dust mites due to natural allelic variation. Any and all such nucleotide variations and resulting amino acid polymorphisms are within the scope of this invention. Furthermore, there may be one or more isoforms or related, cross-reacting family members of Der p VII or Der f VII. Such isoforms or family members are defined as proteins related in function and amino acid sequence to Der p VII or Der f VII, but encoded by genes at different loci.

Fragments of the nucleic acid encoding Der p VII or Der f VII are also within the scope of the invention. As used herein, a fragment of the nucleic acid encoding Der p VII or Der f VII refers to a nucleotide sequence having fewer nucleotides than the nucleotide sequence encoding the entire amino acid sequence of Der p VII or Der f VII protein and which encodes a peptide having an activity of Der p VII or Der f VII (i.e., a peptide having at least one biological activity of the Der p VII or Der f VII allergen) as defined herein.

Preferred nucleic acid fragments encode peptides of at least about 7 amino acid residues in length, preferably about 13–40 amino acid residues in length, and more preferably about 16–30 amino acid residues in length. Nucleic acid fragments which encode peptides having a Der p VII activity of at least about 30 amino acid residues in length, at least about 40 amino acid residues in length, at least about 60 amino acid residues in length, at least about 80 amino acid residues in length, at least about 100 amino acid residues in length, at least about 140 residues in length, and at least about 190 residues in length or more are also within the scope of this invention. Nucleic acid fragments which encode peptides having a Der f VII activity of at least about 30 amino acid residues in length, at least about 40 amino acid residues in length, at least about 60 amino acid residues in length, at least about 80 amino acid residues in length, at least about 100 amino acid residues in length, at least about 140 residues in length, and at least about 200 amino acid residues in length or more are also within the scope of this invention. In general, expression of peptides in a transformed host cell is most advantageous where the desired peptide is greater than about 20 amino acids in length. Shorter peptides are typically more easily synthesized chemically.

Nucleic acid fragments within the scope of the invention include those capable of hybridizing under high or low stringency conditions with nucleic acids from other animal species for use in screening protocols to detect Der p VII or Der f VII or allergens that are cross-reactive with Der p VII or Der f VII. Generally, the nucleic acid encoding a peptide having an activity of Der p VII or Der f VII will be selected from the bases encoding the mature protein, however, in some instances it may be desirable to select all or part of a peptide from the leader sequence portion of the nucleic acids of the invention. Nucleic acids within the scope of the invention may also contain linker sequences, modified restriction endonuclease sites and other sequences useful for molecular cloning, expression or purification of recombinant peptides having an activity of Der p VII or Der f VII.

A nucleic acid encoding a peptide having an activity of Der p VII or Der f VII may be obtained from mRNA of the dust mite *Dermatophagoides pteronyssinus* or *Dermatophagoides farinae*. It should also be possible to obtain nucleic acids encoding Der p VII or Der f VII from *Dermatophagoides pteronyssinus* or *Dermatophagoides farinae* genomic DNA. For example, the gene encoding Der p VII or Der f VII can be cloned from either a cDNA or a genomic library in accordance with protocols herein described (see Examples 1 and 2). A cDNA encoding Der p VII or Der f VII can be obtained by isolating total mRNA from *Dermatophagoides pteronyssinus*. Double stranded cDNAs can then be prepared from the total mRNA. Subsequently, the cDNAs can be inserted into a suitable plasmid or bacteriophage vector using any one of a number of known techniques. Genes encoding Der p VII or Der f VII can also be cloned using established polymerase chain reaction techniques (see Examples 4 and 5) in accordance with the nucleotide sequence information provided by the invention. The nucleic acids of the invention can be DNA or RNA. A preferred nucleic acid is a cDNA encoding Der p VII or Der f VII having the sequence depicted in FIGS. 3A and 3B (SEQ ID NO: 1) (Der p VII ) or FIGS. 6A and 6B (SEQ ID NO: 6) (Der f VII).

This invention also provides expression vectors containing a nucleic acid encoding a peptide having an activity of Der p VII or Der f VII, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of Der p VII or Der f VII. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a DNA encoding a peptide having an activity of Der p VII or Der f VII. Such expression vectors can be used to transfect cells to thereby produce proteins or peptides, including fusion proteins or peptides encoded by nucleic acids as described herein.

This invention further pertains to a host cell transfected to express a peptide having an activity of Der p VII or Der f VII. The host cell may be any procaryotic or eucaryotic cell. For example, a peptide having an activity of Der p VII or Der f VII may be expressed in bacterial cells such as *E. coli*, insect cells (baculovirus), yeast, or mammalian cells such as Chinese hamster ovary cells (CHO). Other suitable host cells can be found in Goeddel, (1990) supra or known to those skilled in the art.

Expression in eucaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *Embo J.*, 6: 229–234), pMFa (Kurjan and Herskowitz, (1982) Cell, 30: 933–943), pJRY88 (Schultz et al., (1987) Gene, 54: 113–123, and pYES2 (Invitrogen Corporation, San Diego, Calif.). Baculovirus vectors available for expression of proteins, in cultured insect cells (SF 9 cells) include the pAc series (Smith et al., (1983) Mol. *Cell Biol.*, 3: 2156–2165) and the pVL series (Lucklow, V. A., and Summers, M. D., (1989) *Virology*, 170: 31–39). Generally COS cells (Gluzman, Y., (1981) Cell, 23: 175–182) are used in conjunction with such vectors as pCDM 8 (Aruffo, A. and Seed, B., (1987) *Proc. Natl. Acad. Sci. USA*, 84: 8573–8577) for transient amplification/expression in mammalian cells, while CHO (dhfr- Chinese Hamster Ovary) cells are used with vectors such as pMT2PC (Kaufmnan et al., (1987) *EMBO J.*, 6: 187–195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al., (*Molecular Cloning: A Laboratory Manual*, 2nd Edition, Cold Spring Harbor Laboratory press (1989)), and other laboratory textbooks.

Expression in procaryotes is most often carried out in *E. coli* with either fusion or non-fusion inducible expression vectors. Fusion vectors usually add a number of NH2 terminal amino acids to the expressed target gene. These NH2 terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene*, 69: 301–315) and pET 11d (Studier et al., *Gene Expression Technology: Methods in Enzymology*, 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant Der p VII or Der f VII expression in *E. coli* is to express the protein in a host bacteria with an impaired capacity to proteolytically cleave the recombinant protein (Gottesman, S., *Gene Expression Technology: Methods in Enzymology*, 185, Academic Press, San Diego, Calif. (1990) 119–128). Another strategy is be to alter the nucleic acid encoding the Der p VII or Der f VII protein to be inserted into an expression vector so that the individual codons for each amino acid would be those preferentially utilized in highly expressed *E. coli* proteins (Wada et al., (1992) *Nuc. Acids Res.*, 20: 2111–2118). Such alteration of nucleic acids of the invention can be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (S e.g., Itakura et al., U.S. Pat. No. 4,598,049; Caruthers et al., U.S. Pat. No. 4,458,066; and Itakura, U.S. Pat. Nos. 4,401,796 and 4,373,071, incorporated by reference herein).

This invention further pertains to methods of producing peptides that have an activity of Der p VII or Der f VII. For example, a host cell transfected with a nucleic acid vector directing expression of a nucleotide sequence encoding a peptide having an activity of Der p VII or Der f VII can be cultured under appropriate conditions to allow expression of the peptide to occur. The peptide may be secreted and isolated from a mixture of cells and medium containing the peptide having an activity of Der p VII or Der f VII. Alternatively, the peptide may be retained cytoplasmically and the cells harvested, lysed and the protein isolated. A cell culture includes host cells, media and other byproducts. Suitable media for cell culture are well known in the art. The peptide having an activity of Der p VII or Der f VII can be isolated from cell culture medium, host cells, or both using techniques known in the art for purifying proteins including ion-exchange chromatography, gel filtration chromatography, ultrafiltration, electrophoresis, and immunoaffinity purification with antibodies specific for a peptide having an activity of Der p VII or Der f VII.

Another aspect of the invention pertains to isolated peptides having an activity of Der p VII or Der f VII. A peptide having an activity of Der p VII or Der f VII has at least one biological activity of the Der p VII or Der f VII allergen. For example, a peptide having an activity of Der p VII or Der f VII may have the ability to induce a response in Der p VII or Der f VII specific T cells such as stimulation (T cell proliferation or cytokine secretion) or to induce T cell non-responsiveness. In one embodiment, a peptide having an activity of Der p VII or Der f VII stimulates T cells as evidenced by, for example, T cell proliferation or cytokine secretion. In another embodiment, peptides having a Der p VII or Der f VII activity induce T cell non-responsiveness in which T cells are unresponsive to a subsequent challenge with a Der p VII or Der f VII peptide following exposure to the peptide. In yet another embodiment, a peptide, having a Der p VII or Der f VII activity has reduced IgE binding activity compared to purified, native Der p VII or Der f VII protein. A peptide having an activity of Der p VII or Der f VII may differ in amino acid sequence from the Der p VII or Der f VII sequence depicted in FIGS. 3A and 3B (SEQ ID NO:2) (Der p VII) or FIGS. 6A and 6B (SEQ ID NO: 7) (Der f VII) but such differences result in a modified protein which functions in the same or similar manner as a native Der p VII or Der f VII protein or which has the same or similar characteristics of a native Der p VII or Der f VII protein. Various modifications of the Der p VII or Der f VII protein to produce these and other functionally equivalent peptides are described in detail herein. The term peptide, as used herein, refers to full length proteins and polypeptides or peptide fragments thereof.

A peptide can be produced by modification of the amino acid sequence of the Der p VII or Der f VII protein shown in FIGS. 3A and 3B (SEQ ID NO: 2) (Der p VII) or FIGS. 6A and 6B (SEQ ID NO: 7) (Der f VII), such as a substitution, addition, or deletion of an amino acid residue which is not directly involved in the function of the protein. Peptides of the invention can be at least about 10 amino acid residues in length, preferably about 10–20 amino acid residues in length, and more preferably about 10–16 amino acid residues in length. Peptides having an activity of Der p VII or Der f VII and which are at least about 30 amino acid residues in length, at least about 40 amino acid residues in length, at least about 60 amino acid residues in length, at least about 80 amino acid residues in length, and at least about 100 amino acid residues in length are also included within the scope of this invention.

Another embodiment of the invention provides a substantially pure preparation of a peptide having an activity of Der p VII or Der f VII. Such a preparation is substantially free of proteins and peptides with which the peptide naturally occurs (i.e., other dust mite peptides), either in a cell or when secreted by a cell.

The term isolated as used herein refers to a nucleic acid or peptide that is substantially free of cellular material or culture medium when produced by recombinant DNA techniques, or chemical precursors or other chemicals when chemically synthesized. Such proteins or peptides are also characterized as being free of all other dust mite proteins. Accordingly, an isolated peptide having an activity of Der p VII or Der f VII is produced recombinantly or synthetically and is substantially free of cellular material and culture medium or substantially free of chemical precursors or other chemicals and is substantially free of all other dust mite proteins. An isolated nucleic acid is also free of sequences which naturally flank the nucleic acid (i.e., sequences located at the 5' and 3' ends of the nucleic acid) in the organism from which the nucleic acid is derived.

Peptides having an activity of Der p VII or Der f VII can be obtained, for example, by screening peptides recombinantly produced from the corresponding fragment of the nucleic acid of Der p VII or Der f VII encoding such peptides. In addition, fragments can be chemically synthesized using techniques known in the art such as conventional Merrifield solid phase f-Moc or t-Boc chemistry. For example, the Der p VII or Der f VII protein may be arbitrarily divided into fragments of desired length with no overlap of the fragments, or preferably divided into overlapping fragments of a desired length. The fragments can be produced (recombinantly or by chemical synthesis) and tested to identify those peptides having a Der p VII or Der f VII activity (i.e., the ability to induce a T cell response such as stimulation (proliferation, cytokine secretion), nonresponsiveness, and/or has reduced IgE binding activity).

In one embodiment, peptides having an activity of Der p VII or Der f VII can be identified by the ability of the peptide to stimulate T cells or to induce T cell non-responsiveness. Peptides which stimulate T cells, as determined by, for example, T cell proliferation or cytokine secretion are defined herein as comprising at least one T cell epitope. T cell epitopes are believed to be involved in initiation and perpetuation of the immune response to the protein allergen which is responsible for the clinical symptoms of allergy. These T cell epitopes are thought to trigger early events at the level of the T helper cell by binding to an appropriate HLA molecule on the surface of an antigen presenting cell, thereby stimulating the T cell subpopulation with the relevant T cell receptor for the epitope. These events lead to T cell proliferation, lymphokine secretion, local inflammatory reactions, recruitment of additional immune cells to the site of antigen/T cell interaction, and activation of the B cell cascade, leading to the production of antibodies. One isotype of these antibodies, IgE, is fundamentally important to the development of allergic symptoms and its production is influenced early in the cascade of events at the level of the T helper cell, by the nature of the lymphokines secreted. A T cell epitope is the basic element, or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Screening peptides for those which retain a Der p VII or Der f VII activity as described herein can be accomplished using one or more of several different assays. For example, in vitro, Der p VII or Der f VII T cell stimulatory activity is assayed by contacting a peptide known or suspected of having a Der p VII or Der f VII activity with an antigen presenting cell which presents appropriate MHC molecules in a T cell culture. Presentation of a peptide having a Der p VII or Der f VII activity in association with appropriate MHC molecules to T cells in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA*, 86: 1333 (1989) the pertinent portions of which are incorporated herein by reference. A kit for an assay for the production of interferon is also available from Genzyme Corporation (Cambridge, Mass.).

Alternatively, a common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

In one embodiment, peptides which have Der p VII or Der f VII T cell stimulating activity (i.e., the peptide comprises at least one T cell epitope) can be identified using an algorithm which predicts the presence of T cell epitopes in a protein sequence, such as the algorithm described by Hill et al., *Journal of Immunology*, 147:189–197 (1991). The algorithm of Hill et al. predicts the location of T cell epitopes in a protein by the presence of certain patterns within the sequence which are likely to bind MHC and therefore may contain T cell epitopes.

In order to determine precise T cell epitopes by, for example, fine mapping techniques, a peptide having Der p VII or Der f VII T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. Following this technique, peptides are selected and produced recombinantly or synthetically. Peptides are selected based on various factors, including the strength of the T cell response to the peptide (e.g., stimulation index), the frequency of the T cell response to the peptide in a population of individuals sensitive to dust mite allergens, and the potential cross-reactivity of the peptide with other dust mite allergens. The physical and chemical properties of these selected peptides (e.g., solubility, stability) are examined to determine whether the peptides are suitable for use in therapeutic compositions or whether the peptides require modification as described herein. The ability of the selected peptides or selected modified peptides to stimulate human T cells (e.g., induce proliferation, lymphokine secretion) is then determined as described herein.

In another embodiment, a peptide having a Der p VII or Der f VII activity is screened for the ability to induce T cell non-responsiveness. The ability of a peptide known to stimulate T cells (as determined by one or more of the above described assays), to inhibit or completely block the activity of purified native Der p VII or Der f VII or portion thereof and induce a state of non-responsiveness can be determined using subsequent attempts at stimulation of the T cells with antigen presenting cells that present native Der p VII or Der f VII or peptide having a Der p VII or Der f VII activity following exposure to the peptide, having a Der p VII or Der f VII activity. If the T cells are unresponsive to the subsequent activation attempts, as determined by interleukin-2 synthesis and/or T cell proliferation, a state of non-responsiveness has been induced. See, e.g., Gimmi et al., (1993) *Proc. Natl. Acad. Sci USA*, 90: 6586–6590; and Schwartz (1990) *Science*, 248 1349–1356, for assay systems that can be used as the basis for an assay in accordance with the present invention.

In yet another embodiment, peptides having a Der p VII or Der f VII activity are identified by IgE binding activity.

For therapeutic purposes, peptides of the invention preferably do not bind IgE specific for a dust mite allergen, or bind such IgE to a substantially lesser extent (e.g., at least 100-fold, less, more preferred at least 1000-fold less) than the corresponding purified native dust mite allergen binds such IgE. Reduced IgE binding activity refers to IgE binding activity that is less than that of purified native Der p VII or Der f VII protein. If a peptide having a Der p VII or Der f VII activity is to be used as a diagnostic reagent, it is not necessary that the peptide have reduced IgE binding activity compared to the native Der p VII or Der f VII allergen. IgE binding activity of peptides can be determined by, for example, an enzyme-linked immunosorbent assay (ELISA) using, for example, sera obtained from a subject, (i.e., an allergic subject) that has been previously exposed to the native Der p VII or Der f VII allergen. Briefly, the peptide suspected of having a Der p VII or Der f VII activity is coated onto wells of a microtiter plate. After washing and blocking the wells, antibody solution consisting of the plasma of an allergic subject who has been exposed to a peptide suspected of having a Der p VII or Der f VII activity is incubated in the wells. The plasma is generally depleted of IgG before incubation. A labeled secondary antibody is added to the wells and incubated. The amount of IgE binding is then quantified and compared to the amount of IgE bound by a purified, native Der p VII or Der f VII protein. Alternatively, the IgE binding activity of a peptide can be determined by Western blot analysis. For example, a peptide suspected of having a Der p VII or Der f VII activity is run on a polyacrylamide gel using SDS-PAGE. The peptide is then transferred to nitrocellulose and subsequently incubated with sera from an allergic subject. After incubation with a labeled secondary antibody, the amount of IgE bound is then determined and quantified.

Another assay which can be used to determine the IgE binding activity of a peptide is a competition ELISA assay. Briefly, an IgE antibody pool is generated by combining plasma from dust mite allergic subjects that have been shown by direct ELISA to have IgE reactive with native Der p VII or Der f VII. This pool is used in ELISA competition assays to compare IgE binding of native Der p VII or Der f VII and a peptide suspected of having a Der p VII or Der f VII activity. IgE binding for the native Der p VII or Der f VII protein and a peptide suspected of having a Der p VII or Der f VII activity is determined and quantified.

If a peptide having an activity of Der p VII or Der f VII binds IgE, and is to be used as a therapeutic agent, it is preferable that such binding does not result in the release of mediators (e.g., histamines) from mast cells or basophils. To determine whether a peptide which binds IgE results in the release of mediators, a histamine release assay can be performed using standard reagents and protocols obtained, for example, from Amac, Inc. (Westbrook, Me.). Briefly, a buffered solution of a peptide suspected of having a Der p VII or Der f VII activity is combined with an equal volume of whole heparinized blood from an allergic subject. After mixing and incubation, the cells are pelleted and the supernatants are processed and analyzed using a radioimmunoassay to determine the amount of histamine released.

Peptides having an activity of Der p VII or Der f VII which are to be used as therapeutic agents are preferably tested in mammalian models of dust mite atopy, such as the mouse model disclosed in Tamura et al., (1986) *Microbiol. Immunol.*, 30: 883–896, or in U.S. Pat. No. 4,939,239, or in the primate model disclosed in Chiba et al., (1990) *Int. Arch. Allergy Immunol.*, 93: 83–88. Initial screening for IgE binding to a peptide having an activity of Der p VII or Der f VII may be performed by scratch tests or intradermal skin tests on laboratory animals or human volunteers, or in in vitro systems such as RAST, RAST inhibition, ELISA assay, RIA (radioimmunoassay), or a histamine release assay, as described above.

It is possible to modify the structure of a peptide having an activity of Der p VII or Der f VII for such purposes as increasing solubility, enhancing therapeutic or prophylactic efficacy, or stability (e.g., shelf life ex vivo and resistance to proteolytic degradation in vivo). Such modified peptides are considered functional equivalents of peptides having an activity of Der p VII or Der f VII as defined herein. A modified peptide can be produced in which the amino acid sequence has been altered, such as by amino acid substitution, deletion, or addition, to modify immunogenicity and/or reduce allergenicity, or to which a component has been added for the same purpose.

For example, a peptide having an activity of Der p VII or Der f VII can be modified so that it maintains the ability to induce T cell non-responsiveness and bind MHC proteins without the ability to induce a strong proliferative response or possibly, any proliferative response when administered in immunogenic form. In this instance, critical binding residues for T cell receptor function can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate, or not affect T cell reactivity. In addition, those amino acid residues which are not essential for T cell receptor interaction can be modified by being replaced by another amino acid whose incorporation may enhance, diminish but not eliminate, or not affect T cell reactivity, but does not eliminate binding to relevant MHC.

Additionally, a peptide having an activity of Der p VII or Der f VII can be modified by replacing an amino acid shown to be essential to interact with the MHC protein complex with another, preferably similar amino acid residue (conservative substitution) whose presence is shown to enhance, diminish but not eliminate, or not affect T cell activity. In addition, amino acid residues which are not essential for interaction with the MHC protein complex but which still bind the MHC protein complex can be modified by being replaced by another amino acid whose incorporation may enhance, not affect, or diminish but not eliminate T cell reactivity. Preferred amino acid substitutions for non-essential amino acids include, but are not limited to substitutions with alanine, glutamic acid, or a methyl amino acid.

Another example of modification of a peptide having an activity of Der p VII or Der f VII is substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the peptide.

In order to enhance stability and/or reactivity, a peptide having an activity of Der p VII or Der f VII can be modified to incorporate one or more polymorphisms in the amino acid sequence of the protein allergen resulting from any natural allelic variation. Additionally, D-amino acids, non-natural amino acids, or non-amino acid analogs can be substituted or added to produce a modified protein within the scope of this invention. Furthermore, a peptide having an activity of Der p VII or Der f VII can be modified using polyethylene glycol (PEG) according to the method of A. Sehon and co-workers (Wie et al., supra) to produce a protein conjugated with PEG. In addition, PEG can be added during chemical synthesis of the protein. Other modifications of a peptide having an activity of Can f Ior Der f VII include reduction/alkylation (Tarr, *Methods of Protein Microcharacterization*, J. E. Silver ed., Humana Press, Clifton N.J. 155-194 (1986)); acylation (Tarr, supra); chemical coupling to an appropriate carrier (Mishell and Shiigi, eds, *Selected Methods in Cellular Immunology*, W H Freeman, San Francisco, Calif. (1980), U.S. Pat. No. 4,939,239; or mild formalin treatment (Marsh, (1971) *Int. Arch. of Allergy and Appl. Immunol.*, 41: 199–215).

To facilitate purification and potentially increase solubility of a peptide having an activity of Der p VII or Der f VII, it is possible to add an amino acid fusion moiety to the peptide backbone. For example, hexa-histidine can be added to the protein for purification by immobilized metal ion affinity chromatography (Hochuli, E. et al., (1988) *Bio/Technology*, 6: 1321–1325). In addition, to facilitate isolation of peptides free of irrelevant sequences, specific endoprotease cleavage sites can be introduced between the sequences of the fusion moiety and the peptide. In order to successfully desensitize a subject to Der p VII or Der f VII protein or related allergen, it may be necessary to increase the solubility of the protein by adding functional groups to the protein, or by omitting hydrophobic regions of the protein. Functional groups, such as charged amino acids and charged amino acid pairs are suitable for increasing solubility when added to the amino or carboxy terminus of the peptide.

To potentially aid proper antigen processing of T cell epitopes within Der p VII or Der f VII, canonical protease sensitive sites can be engineered between regions, each comprising at least one T cell epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more T cell epitopes. In addition, such charged amino acid residues can result in an increase in the solubility of the peptide.

Site-directed mutagenesis of a nucleic acid encoding a peptide having an activity of Der p VII or Der f VII can be used to modify the structure of the peptide by methods known in the art. Such methods may, among others, include polymerase chain reaction (PCR) with oligonucleotide primers bearing one or more mutations (Ho et al., (1989) *Gene*, 77: 51–59) or total synthesis of mutated genes (Hostomsky, Z. et al., (1989) *Biochem. Biophys. Res. Comm*, 161: 1056–1063). To enhance recombinant protein expression, the aforementioned methods can be applied to change the codons present in the cDNA sequence of the invention to those preferentially utilized by the host cell in which the recombinant protein is being expressed (Wada et al., supra).

Another aspect of the invention pertains to an antibody specifically reactive with a peptide having an activity of Der p VII or Der f VII. The antibodies of this invention can be used to standardize allergen extracts or to isolate the naturally-occurring or native form of Der p VII or Der f VII. For example, by using peptides having an activity of Der p VII or Der f VII based on the cDNA sequence of Der p VII or Der f VII, anti-protein/anti-peptide antisera or monoclonal antibodies can be made using standard methods. A mammal such as a mouse, a hamster or rabbit can be immunized with an immunogenic form of the peptide (e.g., Der p VII or Der f VII protein or an antigenic fragment which is capable of eliciting an antibody response). Techniques for conferring immunogenicity on a protein or peptide include conjugation to carriers or other techniques well known in the art. A peptide having an activity of Der p VII or Der f VII can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, anti-Der p VII or anti-Der f VII antisera can be obtained and, if desired, polyclonal anti-Der p VII or anti-Der f VII antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, (1975) *Nature*, 495–497) as well as other techniques such as the human B cell hybridoma technique (Kozbar et al., (1983) *Immunology Today*, 4: 72) and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a peptide having an activity of Der p VII or Der f VII and the monoclonal antibodies isolated.

The term antibody as used herein is intended to include fragments thereof which are also specifically reactive with the peptide having an activity of Dr p VII or Der f VII. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-Der p VII or anti-Der f VII portion.

Another aspect of this invention provides T cell clones and soluble T cell receptors specifically reactive with a peptide having an activity of Der p VII or Der f VII. Monoclonal T cell populations (i.e., T cells genetically identical to one another and expressing identical T cell receptors) can be derived from an individual sensitive to Der p VII or Der f VII, followed by repetitive in vitro stimulation with a Der p VII or Der f VII protein or peptide having an activity of Der p VII or Der f VII in the presence of MHC-matched antigen-presenting cells. Single Der p VII or Der f VII MHC responsive cells can then be cloned by limiting dilution and permanent lines expanded and maintained by periodic in vitro restimulation. Alternatively, Der p VII or Der f VII specific T-T hybridomas can be produced by a technique similar to B cell hybridoma production. For example, a mammal, such as a mouse, is immunized with a peptide having an activity of Der p VII or Der f VII, T cells are then purified and fused with an autonomously growing T cell tumor line. From the resulting hybridomas, cells responding to a peptide having an activity of Der p VII or Der f VII are selected and cloned. Procedures from propagating monoclonal T cell populations are described in *Cellular and Molecular Immunology* (Abul K. Abbas et al. ed.), W. B. Saunders Company, Philadelphia, Pa. (1991) page 139. Soluble T cell receptors specifically reactive with a peptide having an activity of Der p VII or Der f VII can be obtained by immunoprecipitation using an antibody against the T cell receptor as described in *Immunology: A Synthesis* (Second Edition), Edward S. Golub et al., ed., Sinauer Associates, Inc., Sunderland, Mass. (1991) pages 366–269.

T cell clones specifically reactive with a peptide having an activity of Der p VII or Der f VII can be used to isolate and molecularly clone the gene encoding the relevant T cell receptor. In addition, a soluble T cell receptor specifically reactive with a peptide having an activity of Der p VII or Der f VII can be used to interfere with or inhibit antigen-dependent activation of the relevant T cell subpopulation, for example, by administration to an individual sensitive to Der p VII or Der f VII. Antibodies specifically reactive with such a T cell receptor can be produced according to the techniques described herein. Such antibodies can be used to block or interfere with the T cell interaction with peptides presented by MHC.

Exposure of allergic subjects to peptides having an activity of Der p VII or Der f VII and which have T cell stimulating activity, may cause the appropriate T cell subpopulations to become non-responsive to the respective protein allergen (e.g., fail to stimulate an immune response upon such exposure). In addition, such administration may modify the lymphokine secretion profile as compared with exposure to the naturally-occurring protein allergen or portion thereof (e.g., result in a decrease of IL-4 and/or an increase in IL-2). Furthermore, exposure to peptides having an activity of Der p VII or Der f VII which have T cell stimulating activity may influence T cell subpopulations which normally participate in the response to the allergen such that these T cells are drawn away from the site(s) of normal exposure to the allergen (e.g., nasal mucosa, skin, and lung) towards the site(s) of therapeutic administration of the protein or fragment derived therefrom. This redistribution of T cell subpopulations may ameliorate or reduce the ability of an individual's immune system to stimulate the usual immune response at the site of normal exposure to the allergen, resulting in a diminution in allergic symptoms.

A peptide having an activity of Der p VII or Der f VII when administered to a subject sensitive to dust mite allergens is capable of modifying the B cell response, T cell response, or both the B cell and the T cell response of the subject to the allergen. As used herein, modification of the allergic response of a subject to a dust mite allergen can be defined as non-responsiveness or diminution in symptoms to the allergen, as determined by standard clinical procedures (See e.g., Varney et al., (1990) *British Medical Journal*, 302: 265–269), including diminution in dust mite induced asthmatic symptoms. As referred to herein, a diminution in symptoms includes any reduction in the allergic response of a subject to the allergen following a treatment regimen with a peptide of the invention. This diminution in symptoms may be determined subjectively (e.g., the patient feels more comfortable upon exposure to the allergen), or clinically, such as with a standard skin test.

Peptides or antibodies of the present invention can also be used for detecting and diagnosing sensitivity to Der p VII or Der f VII. For example, this can be done in vitro by combining blood or blood products obtained from a subject to be assessed for sensitivity with peptide having an activity of Der p VII or Der f VII, under conditions appropriate for binding of components in the blood (e.g., antibodies, T cells, B cells) with the peptide(s) and determining the extent to which such binding occurs. Other diagnostic methods for allergic diseases which the peptides or antibodies of the present invention can be used include radio-allergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The present invention further provides methods of detecting and treating sensitivity in a subject to Der p VII or Der f VII. The presence in subjects of IgE specific for Der p VII or Der f VII and the ability of T cells of the subjects to respond to T cell epitopes of Der p VII or Der f VII can be determined by administering to the subject an Immediate Type Hypersensitivity test and/or a Delayed Type. Hypersensitivity test (See e.g., Immunology (1985) Roitt, I. M., Brostoff, J., Male, D. K. (eds), C. V. Mosby Co., Gower Medical Publishing, London, N.Y., pp. 19.2–19.18; pp.22.1–22.10) utilizing a peptide having an activity of Der p VII or Der f VII, or a modified form of a peptide having an activity of Der p VII or Der f VII, each of which binds IgE specific for the allergen. The same subjects are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those subjects exhibiting a specific Immediate Type Hypersensitivity reaction. The Delayed Type Hypersensitivity test utilizes a peptide having an activity of Der p VII or Der f VII which has human T cell stimulating activity and which does not bind IgE specific for the allergen in a substantial percentage of the population of subjects sensitive to the allergen (e.g., at least about 75%). Those subjects found to have both a specific Immediate type Hypersensitivity reaction and a specific Delayed Type Hypersensitivity reaction are administered an amount of a composition suitable for pharmaceutical administration. The composition comprises the peptide having an activity of Der p VII or Der f VII as used in the Delayed Type Hypersensitivity test and a pharmaceutically acceptable carrier or diluent.

A peptide having an activity of Der p VII or Der f VII can be used in methods of diagnosing, treating, or preventing allergic reactions to a dust mite allergen or a cross-reactive protein allergen. Thus, the present invention provides compositions suitable for in vitro use and pharmaceutical administration comprising an amount of at least one peptide having an activity of Der p VII or Der f VII. Pharmaceutical compositions typically will be formulated with a pharmaceutically acceptable carrier.

Where a composition according to the invention is intended for administration to a subject to be desensitized, such administration can be carried out using known procedures, at dosages and for periods of time effective to reduce sensitivity (i.e., reduce the allergic response) of the subject to a dust mite allergen. The term subject is intended to include living organisms in which an immune response can be elicited, e.g., mammals. Examples of subjects include humans, dogs, cats, mice, rats, and transgenic species thereof. An amount of at least one peptide having an activity of Der p VII or Der f VII necessary to achieve a therapeutic effect may vary according to factors such as the degree of sensitivity of the subject to dust mite, the age, sex, and weight of the subject, and the ability of a peptide having an activity of Der p VII or Der f VII to elicit an antigenic response in the subject. Dosage regima may be adjusted to provide the optimum therapeutic response. For example, several divided doses may be administered daily or the dose may be proportionally reduced as indicated by the exigencies of the therapeutic situation.

The active compound (i.e., a peptide having an activity of Der p VII or Der f VII) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a peptide having an activity of Der p VII or Der f VII by other than parenteral administration, it may be necessary to coat the peptide with, or co-administer the peptide with, a material to prevent its inactivation. For example, a peptide having an activity of Der p VII or Der f VII may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.*, 2: 27). For purposes of inducing T cell nonresponsiveness, the composition is preferably administered in non-immunogenic form, e.g., one that does not contain adjuvant.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (i.e., a peptide having an activity of Der p VII or Der f VII) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., at least one peptide having an activity of Der p VII or Der f VII) plus any additional desired ingredient from a previously sterile-filtered solution thereof.

When the peptide having an activity of Der p VII or Der f VII is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 5 to about 80% of the weight of the unit. The amount of active compound in such therapeutically useful compositions is such that a suitable dosage will be obtained.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in subjects.

The present invention also provides a composition comprising at least two peptides having an activity of Der p VII or Der f VII (e.g., a physical mixture of at least two peptides), each having T cell stimulating activity. For example, at least two peptides each having as activity of Der p VII can be combined or at least two peptides each having an activity of Der f VII can be combined, or at least one peptide having an activity of Der p VII and at least one peptide having an activity of Der f VII can be combined and administered. Alternatively, a peptide having at least two regions, each having T cell stimulating activity (i.e., each region comprising at least one T cell epitope) can be administered to an allergic subject. Such a peptide can have at least two regions derived from the same allergen, Der p VII or Der f VII, or a combination of Der p VII and Der f VII. A composition of two peptides or a peptide having at least two regions can be administered to a subject in the form of a composition with a pharmaceutically acceptable carrier as hereinbefore described. An amount of one or more of such compositions can be administered simultaneously or sequentially to a subject sensitive to a dust mite allergen to treat such sensitivity. Such compositions may be useful for the manufacture of a medicament for treating sensitivity to house dust mites in an individual.

The cDNA (or the mRNA which served as a template during reverse transcription) encoding a peptide having an activity of Der p VII or Der f VII can be used to identify similar nucleic acid sequences in any variety or type of animal and, thus, to molecularly clone genes which have sufficient sequence homology to hybridize to the cDNA encoding a peptide having an activity of Der p VII or Der f VII. Thus, the present invention includes not only peptides having an activity of Der p VII or Der f VII, but also other proteins which may be allergens encoded by DNA which hybridizes to DNA of the present invention.

Isolated peptides that are immunologically related to Der p VII or Der f VII, such as by antibody cross-reactivity or T cell cross-reactivity, other than those already identified, are within the scope of the invention. Such peptides bind antibodies specific for the protein and peptides of the invention, or stimulate T cells specific for the protein and peptides of this invention.

A peptide having an activity of Der p VII or Der f VII (i.e., Der p VII or Der f VII produced recombinantly or by chemical synthesis) is free of all other dust mite proteins and, thus, is useful in the standardization of allergen extracts which are key reagents for the diagnosis and treatment of dust mite hypersensitivity. In addition, such a peptide is of a consistent, well-defined composition and biological activity for use in preparations which can be administered for therapeutic purposes (e.g., to modify the allergic response of a subject sensitive to dust mite). Such peptides can also be used to study the mechanism of immunotherapy of *Dermatophagoides pteronyssinus* and *Dermatophagoides farinae* allergy and to design modified derivatives or analogs useful in immunotherapy.

Work by others has shown that high doses of allergen extracts generally produce the best results during immunotherapy (i.e., best symptom relief). However, many subjects are unable to tolerate large doses of such extracts due to systemic reactions elicited by the allergens and other components within these preparations. A peptide having an activity of Der p VII or Der f VII according to the invention has the advantage of being free of all other dust mite proteins, and thus are safer and more suitable for therapeutic uses.

It is now also possible to design an agent or a drug capable of blocking or inhibiting the ability of a dust mite allergen to induce an allergic reaction in sensitive subjects. Such agents could be designed, for example, in such a manner that they would bind to relevant anti-Der p VII or anti-Der f VII IgE molecules, thus preventing IgE-allergen binding, and subsequent mast cell/basophil degranulation. Alternatively, such agents could bind to cellular components of the immune system, resulting in suppression or desensitization of the allergic responses to dust mite allergens. A non-restrictive example of this is the use of peptides including B or T cell epitopes of Der p VII or Der f VII, or modifications thereof, based on the cDNA protein structure of Der p VII or Der f VII to suppress the allergic response to a dust mite allergen. This could be carried out by defining the structures of fragments encoding B and T cell epitopes which affect B and T cell function in in vitro studies with blood components from subjects sensitive to dust mite.

The invention is further illustrated by the following examples which should not be construed as further limiting the subject invention. The contents of all references and published patent applications cited throughout this application are hereby incorporated by reference.

EXAMPLE 1

Isolation of Clone HD6 from a λgt11 cDNA Library

A λgt11 cDNA library was prepared from live adult *Dermatophagoides pteronyssinus* purchased from the Commonwealth Serum Laboratories, Parkville, Australia (Thomas, W., et al., *Int Arch Allergy Appl Immunol* (1988) 85:127–9). The library was prepared according to Chua et al. (J. Exp. Med. (1988) 167:175–182) based upon the method of Young and Davis (*Proc. Natl. Acad. Sci. USA* (1983) 80:1194–1198) and Gubler and Hoffmnan (Gene (1983) 2:263–299). Polyadenylated mRNA was isolated from a *D. pteronyssinus* culture and cDNA synthesized by the RNaseH method (Gubler and Hoffmnan, supra) using a kit (Amersham International, Bucks). After the addition of EcoRI linkers the cDNA was ligated into λgt11 and plated in *E. coli* Y1090 (r–) (Promega Biotec, Madison, Wis.) to produce a library of $5 \times 10^5$ recombinants.

Allergic serum was used to probe the λgt11 library. IgE plaque immunoassays were conducted by a standard procedure (Chua, K. Y., et al., *Int Arch Allergy Appl Immunol* (1990) 91:118–23) using 20 000 pfu on 14.5 cm petri dishes. Briefly, an overnight culture of *E. coli* Y1090 (Huynh, T. V. et al. Constructing and Screening cDNA Libraries in gt10 and gt11 in: *A Practical Approach*, Oxford IRL Press, 1986, pp 48–78) was diluted 1/50 in L broth and incubated at 37° C. to an $OD_{650}$ of 0.6. The bacteria were pelleted and resuspended in 400 μl for every 50 ml of broth. For 14.5-cm Petri dishes, 300 μl of Y1090 were incubated with $10^4$ pfu phage for 30 minutes at room temperature and then plated on LB agar in 9 ml of 0.7% agar overlay and incubated for 3 hours at 42° C. (when plaques usually become visible). At this time a nitrocellulose filter, which had been saturated with 10 mM isopropyl β-D-thiogalactoside and dried, was placed on top of the lawn. The incubation continued overnight at 37° C. The filter was then removed and washed in 0.01 M Tris-hydrochloride, 0.15 M NaCl, 0.05% Tween 20 v/v, pH 8, (TNT) buffer with gentle rocking for 20 minutes. The filter was then incubated with sera from mite allergic children for 2 hours at room temperature with rocking and then washed three times for 30 minute periods with TNT. The sera used was first diluted 50:50 with an *E. coli* extract (Huynh et al., supra), incubated overnight then clarified by centrifugation (3,000 g 10 minutes). Non-fat milk and sodium azide were added to 5 and 0.02%, respectively. To develop the IgE reactivity the filter was rocked in a solution of $^{125}$I-labelled anti-IgE for 2 hours at room temperature followed by three 30-minute washes with TNT. The anti-IgE was a mouse monoclonal 2.1.5 (available from Silenus Laboratories Pty. Ltd., Hawthorn, Victoria) and was used at 30 ng/ml coupled with $10^5$ dpm/ng $^{125}$I in TNT (Stewart, G. A., et al. *Int. Arch. Allergy Appl. Immunol.* (1988) 86:9–18). It was labelled by the chloramine T method. The filter was autoradiographed with intensifying screens, usually for 48 hours at –70° C.

A λgt11 derived clone HD6 from the *D. pteronyssinus* cDNA library was plaque purified (see Maniati et al. Molecular Cloning: A Laboratory Manual, (1982) Cold Spring Harbor) because it showed high IgE binding activity to a mite allergic serum (obtained from a child attending the allergy clinic at the Taiwan University Hospital, Taipei, R.O.C.) by the plaque radioimmune assay described above. To determine the number of sera with IgE binding for this clone, the λgt11-HD6 was plated at 1 000 pfu on a 90 cm petri dish and a nitrocellulose lift prepared for an immunoassay as outlined in Young and Davis (1983) supra, with modifications as detailed in Chua et al. *Int. Arch. Allergy Appl. Immunol.* (1990) 91:118–123. The filter was cut into segments and IgE immunoassays performed with 20 individual sera obtained from the Royal Children's Hospital Melbourne (Dr. D. Hill) (FIG. 1). Strong reactivity was found with 6 sera and in another series with 8/18. A hyper IgE serum tested at 1 000 IU/ml did not show binding, nor did a serum from a child allergic to only rye grass (see bottom two segments in right-hand column of FIG. 1).

To estimate the size of the IgE binding molecule encoded by the phage, DNA from purified clones was isolated by a polyethyleneglycol precipitation procedure (Chua, K. Y. et al. *J. Exp. Med.* (1988) 167:175–182) and the 812 bp DNA insert found in the λgt11-HD6 was released by EcoRI digestion (Toyobo, Osaka, Japan) and subcloned into the same site in the glutathione-S-transferase fusion vector pGEX-1 (Smith, D. B. et al., *Gene* (1988) 67:31–40) and used to transform *E. coli* TG-1. The protein expressed by this construct was isolated from crude bacterial lysates under non-denaturing conditions by affinity chromatography on immobilized a glutathione (as described in Smith et al. *Gene* (1988) 67:31–40). The fusion protein was then examined by Western blotting. For Western Blot Analysis, proteins were transferred to nitrocellulose (Bio-Rad transblot) by the protocol of Burnette (Burnette, W. N., *Anal Biochem* (1981) 112:195–203) and immunoassays were performed as for the plaque radioimmune assays with allergic sera and $^{125}$j-anti IgE or with rabbit antibodies and $^{125}$I-protein A as described in Greene, W. K., et al., *Int Arch Allergy Appl Immunol* (1990) 92:30–8.

Figure 2:
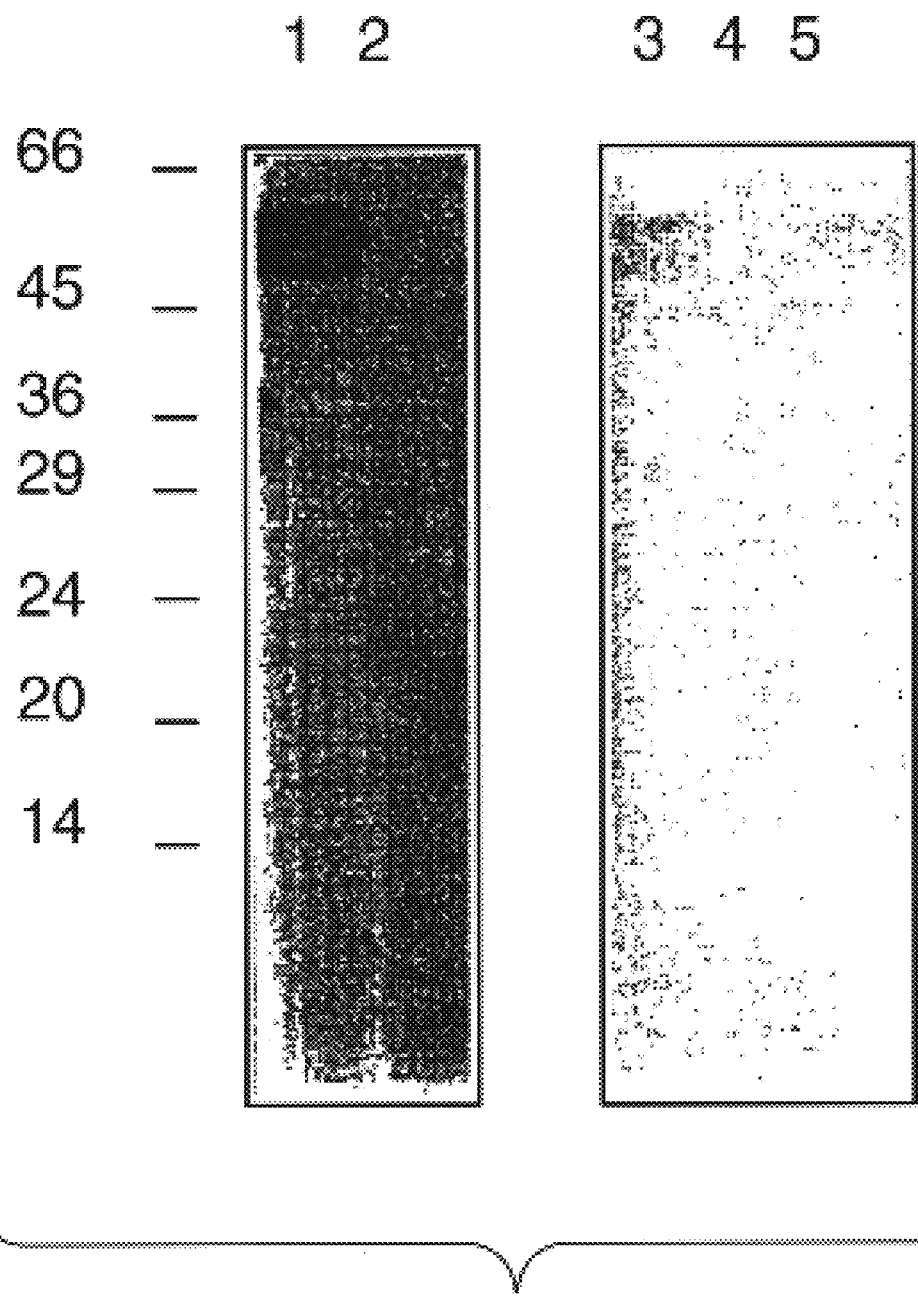
FIG. 2 shows the reactivity of IgE and rabbit anti-house dust mite antibody to purified glutathione-S-transferase fusion product of the HD6 insert cloned into pGEX-1.

Expression in pGEX-1 resulted in a protein(s) which migrated as a doublet with a Mr of 53–55 K and reacted by Western blotting with rabbit anti-house dust mite serum (FIG. 2, lane 1). Two allergic sera reacted with this doublet (FIG. 2, lanes 3 and 5) but not to a hyper IgE serum at 1000 IU/ml (FIG. 2, lane 4) or normal rabbit serum (FIG. 2, lane 2). The IgE binding protein, allowing for the contribution of the 27 K glutathione transferase would therefore be about Mr 27. This, as will be described below, contains residues from the leader sequence and those from the 5' untranslated region.

EXAMPLE 2

DNA Sequence Analysis of Clone HD6

The 812 bp insert of clone HD6 was cloned into the M13 vectors mp18 and mp19 (see Messing *Methods Enzymology* (1983) 101:20) for sequencing performed in both directions using –40, universal and internal primers (Messing, supra). Dideoxynucleotide sequencing (Sambrook, J., et al. *Molecular Cloning. A Laboratory Manual*. 2nd Edition. Cold Spring Harbor: Cold Spring Harbor Laboratory Press, 1989) was performed using a Sequenase 2.0 kit (IBI, New Haven, USA) with $^{32}$P-dATP and a Biorad Sequi-gen electrophoresis apparatus. Following sequence analysis with the universal and internal primers, three primers based on the cDNA sequence of Der p VII were produced and sequencing conducted. The sequences of the primers are as follows: (1)

GATCCAATTCACTATGAT,(bases 119–136 in FIG. 3, SEQ ID NO:3); (2) GGTGAATTAGACATGCG (bases 272–288 in FIGS. 3, SEQ ID NO:4); and (3) TCAATTTTGGATC-CAATTTTCGCT (bases 584–607, SEQ ID NO:5).

The DNA insert was found to have 812 bases with an open reading frame beginning at the 5' end, consistent with its expression as a fusion from λgt11 and pGEX-1, and ending at a stop codon TAG (713–715) (FIG. 3). The sequence of the translated protein appeared to begin at the adjacent initiation ATGs at nucleotides 68–70 and 71–73. This is followed by nucleotides encoding a typical, predominantly hydrophobic, leader sequence (Von Hiejne, G. *J. Mol. Biol.* (1985) 184:99–105) predicted to be 17 residues long, and then a sequence encoding a further 198 residues ending at the TAG codon at nucleotides 713–715. This reading frame was confirmed by using PCR (as described in Saiki et al. Science (1988) 239:487–491) to clone DNA encoding an antigenic product of the correct Mr in pGEX starting at the predicted N-terminal Asp encoded by nucleotide 119–121. The fusion protein from this construct was produced at far higher yields than the fusion which contained the leader peptide (pGEX-1). The 3' untranslated region contained a polyadenylation signal AATAAA at 765–770 (underlined in FIGS. 3) and a polyA tail. A potential N-glycosylation site, Asn Ala Thr, is encoded by nucleotides 518–526 (see FIGS. 3 underlined). No homology was found to sequences in the Genpept 71.0, EMBL 30.0 and Swiss-Prot 21 databases. The predicted molecular weight of the translated polypeptide was 23,865 daltons and 22,177 daltons without the leader sequence.

EXAMPLE 3

Nature of the Allergen Der p VII in Mite Extracts

Figure 4:
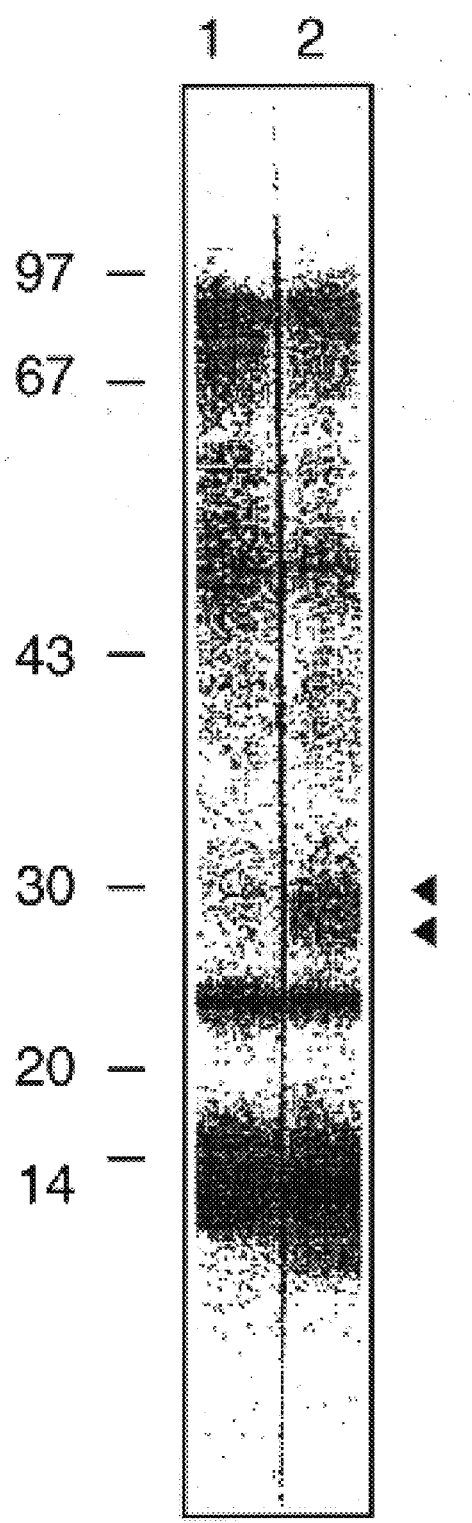
FIG. 4 shows extracts of house dust mites electrophoresed on a 8–18% SDS-PAGE, electroblotted onto nitrocellulose and reacted with pooled allergic serum absorbed with lysates from E coli containing a pGEX-1 vector control (lane 1) or pGEX-1 HD6 (lane 2).

As a first step to identifying the Der p VII native protein allergen, a pool of allergic serum obtained as described previously was absorbed with an equal volume of pGEX-1 HD6 lysate or a control vector lysate (Greene and Thomas *Molec. Immunol.* (1992) 29:259–262). The serum was then used for IgE Western blotting of house dust mite extracts separated by SDS-PAGE performed according to Laemmli (Laemmli, U.K., Nature (1970) 227:680–5) with an 8–18% gradient in 10–12 cm gel assemblies or 13% mini protean II apparatus (Bio-Rad, Richmond, Va., USA). For dust mite extracts, samples were loaded at 0.1 mg protein/track. For bacteria, cultures were centrifuged and the pellets suspended at 0.01 of the culture volume and 10 µl added to sample buffer for electrophoresis. Purified proteins were electrophoresed at 2–5 µl/track. Compared to the serum absorbed with vector control (FIG. 4, lane 2), the HD6 fusion protein absorbed serum (FIG. 4, lane 1) showed a loss of reactivity to bands with Mr of 29, 27 and 11.5 K.

To examine this further, rabbit antibodies to the HD6 protein were affinity purified from a hyperimmune serum using nitrocellulose filters lifted from plates confluent with λgt11-HD6 plaques. Briefly, antibodies with specificities for the allergen expressed by the λgt11 clones were isolated from a hyperimmune rabbit anti-*D. pteronyssinus* serum (Greene, W. K., et al., *Int Arch Allergy Appl Immunol* (1990) 92:30–8) (produced by repeated injections into a rabbit of mite extract) by affinity purification using a nitrocellulose filter blotted on a plaque lawn (Ozaki, L. S., et al., *J. Immunol Methods* (1986) 89:213–9) as the absorbant. λgt11 derived phage (clone HD6) were plated at 10 000 pfu per 90 cm petri dishes and overlaid with nitrocellulose saturated with isopropyl-β-D-thiogalactopyranoside (IPTG) under the same conditions used to screen the library. After overnight incubation, the filter was flipped to expose the other side to the lawn and incubated for 2 hours at 37° C. The filter was then washed in the TNT buffer, (0.01 M Tris hydrochloride, 0.15 NaCl, 0.05% Tween 20 v/v pH 8.0). One ml of rabbit antiserum which had been incubated overnight in 1 ml of a lysate of λgt11 lysogen was diluted to 20 mls with TNT and skim milk powder added to 5%. Aliquots of 5 ml were then rocked in petri dishes containing the filters for 1 hour at room temperature. The filters were washed three times in TNT and incubated for 15 minutes at room temperature in 0.1 M glycine, 0.15 M NaCl pH2.6 to elute the antibodies. Each 5 ml eluate was then neutralized by adding 650 µl of 100 mM Tris and 1.5 m NaCl, 50 ml 1% sodium azide and 0.25 g skim milk. The solution was dialysed against PBS.

Figure 5:
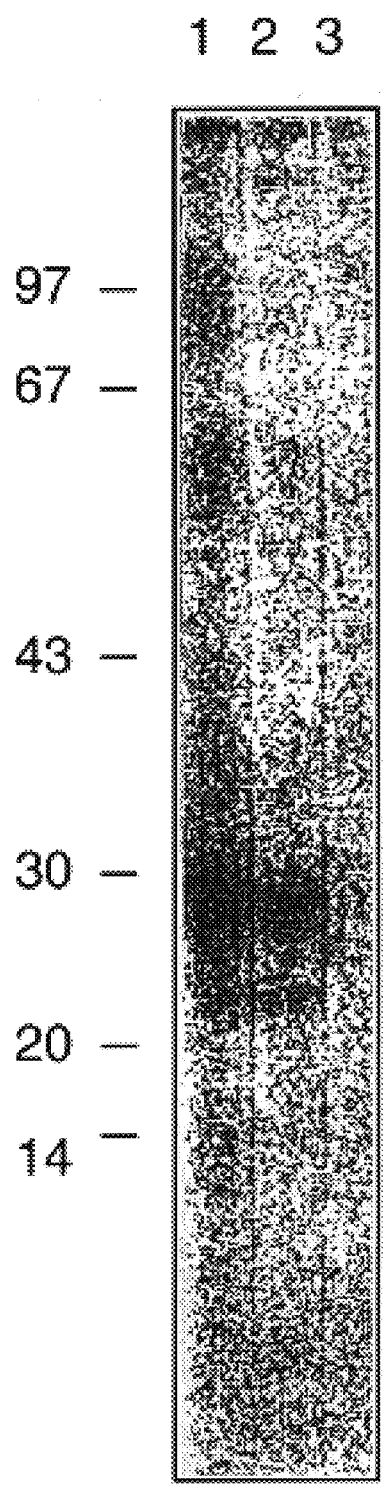
FIG. 5 shows the reactivity of affinity purified anti-HD6 antibodies to D. pteronyssinus extracts. Rabbit antibodies were affinity purified on nitrocellulose and used to probe a Western blot of mite extracts, electrophoresed on 8–18% SDS-PAGE and developed with $125_{I\text{-}protein}$ A.

The affinity purified antibody was then absorbed with *E. coli* lysate used to develop Western blots as described, on the house dust mite extract and found to react with bands of Mr 29, 27 and 24 (FIG. 5). The specificity of the reactivity was further checked by absorbing the affinity purified antibodies with a pGEX-HD6 lysate expressing the protein (FIG. 5, lane 3) or a control pGEX construct, pQEX-D15 (FIG. 5, lane 2). The serum absorbed with HD6 (lane 3) lost reactivity to all bands. The affinity purification therefore shows that antibodies to the allergen have specificities for components at Mr 29, 27 and 24 K. The same pattern of multiple binding to that described above with extracts prepared from CSL mites was also found with another extract from Hollister-Stier Laboratories, Spokane, Wash., USA.

The finding that antibodies to the HD6 lysate reacted specifically to at least 3 bands on Western blotting has implications for determining the number of allergens recognized by individual mite allergic patients. The multiple bands were found for the two independent extracts examined and the absorption studies with allergic serum showed that the 29 and 27 K bands had IgE reactivity and that this recombinant molecule appeared to absorb out all of the reactivity to each band. It is not, however, known from this investigation if all patients react with each band. Because the Western analysis was performed using reducing conditions and the bands had Mr greater than that calculated from the translated sequence, the different forms of the allergens may be interpreted as different glycosylation products. This can be confirmed with some caution taken to control for denaturation by the deglycosylation procedures. The pattern nevertheless indicates that the number of allergic specificities is less than that indicated by electrophoretic procedures, a significant observation for immunotherapeutic strategies using purified, recombinant or peptide allergens. Alternatively, the different Mr bands reacting with the anti-HD6 antibody may indicate the presence of related or cross reactive allergens.

EXAMPLE 4

Isolation of a cDNA Clone Encoding Der f VII from a λgt11 cDNA Library

A λgt11 cDNA library was prepared from live adult *Dermatophagoides farinae* purchased from the Commonwealth Serum Laboratories, Parkville Australia (Thomas, W. et al, *Int. Arch Allergy Appl Immunol* (1988) 85:127–9). The library was prepared according to Trudinger et al., (1991) Chem. Exp. Allergy, 21:33–37).

PCR amplification and DNA sequencing were used to isolate Der f VII cDNA from the λgt11 library. An oligonucleotide primer (Df1 in Table 1) based on the predicted N-terminal sequence of Der p VII was made. This primer had the sequence GCGAATTCGATCCAATTCACTATGAT-3' (SEQ ID NO: 8). The first GCGAATTC encodes an EcoRI site (GAATTC) and the sequence GAT encodes the first six residues of Der p VII. For the other primer, the λgt11 GGTGGCGACGACTCCTGGAGCCCG-3' (SEQ ID NO: 9) forward primer (Df2 in Table 1) flanking the EcoRI cloning site was used (New England Biolabs, Beverly, U.S.A.).

The PCR reactions were carried out in a final reaction volume of 50 μl containing 20 mM Tris-HC1 pH 8.2, 10 mM KC1, 6 mM $(NH_4)_2SO_4$, 2 mM $MgCl_2$, 0.1% Triton X-100, 10 ngμ nuclease-free BSA, 10 mM dNTPs, 20 pmol of each primer and 2.5 units of Pfu DNA polymerase. This was obtained as a kit from Stratagene (La Jolla, Calif., U.S.A.). Target DNA (λgt11 D. farinae cDNA ligations, 0.001 μg) was added and the contents of the tube were mixed and overlayed with paraffin oil. The tubes were initially denatured at 95° C. for 5 min., then annealed at 55° C. for 2 min. and extended at 72° C. for 2 min. Thereafter for 48 cycles, denaturing was carried out for 1 min. at 94° C. and annealing for 1 min. at 55° C. and extension as before. In the final (50th) cycle, the extension reaction was increased to 10 min. to ensure that all amplified products were full length.

Ten microlitres of the reaction were then checked for amplified bands on a 1% agarose gel. The remainder of the reaction mixture was ethanol precipitated prior to purification of the amplified product on a low melting point agarose gel (Bio-Rad., Richmond, U.S.A.).

The purified PCR product was digested with EcoRI and was ligated into the M13 vector mp 18 (see Messing, supra), digested with EcoRi and then transferred into E. coli strain TG1 competent cells. Isolated white plaques were picked and used to prepare phage stocks and single-stranded DNA for sequencing.

EXAMPLE 5

DNA Sequence Analysis of Der f VII cDNA

DNA sequencing was performed with the dideoxynucleotide chain termination method using Sequenase version 2.0 (USB Corp., Cleveland, U.S.A.) according to the supplier's protocol. The primers used for sequencing include the M13 sequencing primer (−40) a 17-mer GTTTTCCCAGTCACGAC-3' (SEQ ID NO: 10) (Df3 in Table 1), the primer Df1 (SEQ ID NO: 8) used for PCR reaction described in Example 4, and 2 other oligonucleotide primers, Df4 and Df5, both shown in Table 1. The primer Df4 GGTGAATTAGCCATGCG-3' (SEQ ID NO: 11) was previously used for the sequencing of Der p VII and primer Df5 TCAATCTTGGATCCAATTTTTGGC-3' (SEQ ID NO: 12) was based on sequences of Der f VII from nucleotides 559–582.

To isolate a cDNA containing the 5' untranslated region of Der f VII, an oligonucleotide primer based on the C terminal sequence of Der f VII was made. This primer (Df6 in Table 1) had the sequence GGAATTCTTAATTTTTTTCCAATTCACG-3' (SEQ ID NO: 13). The first GGAATTC encodes a EcoRI site. This sequence and the following sequence (TTA . . . ). are complementary to the reverse sequences of the stop codon and the last six residues of Der f VII. For the other primer, the λgt11 TTGACACCAGACCAACTGGTAATG-3' reverse primer (SEQ ID NO: 14) (Df7 in Table 1), flanking the EcoRI cloning site, was used.

The PCR reactions were carried out according to conditions described in Example 4. The PCR product was purified on a low melting point agarose gel, digested with EcoRI and was ligated into pUC 19 digested with EcoRI and then transferred into E. coli strain TGI competent cells. Plasmid DNA from transformant E. coli was isolated and used for sequencing.

DNA sequencing was performed using the same dideoxynucleotide chain termination method, Sequence version 2.0, described above. However, before sequencing, the double-stranded plasmid DNA templates were denatured by treatment with NaOH and neutralized by the addition of sodium acetate and then ethanol precipitated according to the supplier's protocol. To obtain the 5' untranslated end of Der f VII cDNA, the primer Df8 (see Table 1) was used. This primer had the sequence ATGACGTTCGAATTTATC-3' (SEQ ID NO: 15) which corresponds to the reverse sequence of Der f VII from nucleotide no. 225–208.

TABLE 1

Oligonucleotides used for PCR amplication and sequencing

| Name | Sequence | | derived from Der f VII nucleotide positions |
|---|---|---|---|
| Df1 | GCGAATTCGATCCAATTCACTATGAT-3' | (SEQ ID NO:8) | 94–111 |
| Df2 | GGTGGCGACGACTCCTGGAGCCCG-3' | (SEQ ID NO:9) | lambda gt11 forward primer |
| Df3 | GTTTTCCCAGTCACGAC-3' | (SEQ ID NO:10) | M13 sequencing primer (−40) |
| Df4 | GGTGAATTAGACATGCG-3' | (SEQ ID NO:11) | 247–263 |
| Df5 | TCAATCTTGGATCCAATTTTTGGC-3' | (SEQ ID NO:12) | 559–582 |
| Df6 | CGAATTCTTAATTTTTTTCCAATTCACG-3' | (SEQ ID NO:13) | 684–664 |
| Df7 | TTGACACCAGACCAACTGGTAATG-3' | (SEQ ID NO:14) | lambda gt11 reverse primer |
| Df8 | ATGACGTTCGAATTTATC-3' | (SEQ ID NO:15) | 225–208 |

Equivalents

Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. An isolated Group VII protein allergen of *Dermatophagoides farinae*, Der f VII, comprising the amino acid sequence shown in FIGS. 6A and 6B (SEQ ID NO:7) or the mature portion thereof.

2. A composition comprising the Der f VII protein allergen of claim 1 and a pharmaceutically acceptable carrier.

3. An isolated Group VII protein allergen of *Dermatophagoides farinae*, Der f VII, encoded by the nucleic acid shown in FIGS. 6A and 6B (SEQ ID NO: 6).

4. An isolated Group VII protein allergen of *Dermatophagoides farinae*, Der f VII, encoded by the nucleotide bases 43 through 681 of the nucleic acid shown in FIG. 6A and 6B (SEQ ID NO: 6).

5. A composition comprising the Der f VII protein allergen of either claim 3 or claim 4 and a pharmaceutically acceptable carrier.

6. The isolated peptide of claim 1, produced by chemical synthesis.

7. The isolated peptide of claim 1, produced by recombinant expression.

8. A method of producing an isolated Group VII protein allergen of *Dermatophagoides farinae*, Der f VII, or the mature portion thereof, the method being selected from the group consisting of:

a) recombinantly producing the protein a host cell transformed with a nucleic acid encoding a Der f VII protein allergen comprising the amino acid sequence shown in FIGS. 6A and 6B (SEQ ID NO:7), or the mature portion thereof; and b) chemically synthesizing the protein, wherein the protein comprises the amino acid sequence shown in FIGS. 6A and 6B (SEQ ID No: 7) or the mature protein thereof.

9. The method of claim 8 wherein the nucleic acid comprises the nucleotide sequence shown in FIGS. 6A and 6B (SEQ ID NO: 6).

\* \* \* \* \*